(12) United States Patent
Banville et al.

(10) Patent No.: US 7,494,984 B2
(45) Date of Patent: Feb. 24, 2009

(54) SUBSTITUTED IMIDAZO[1,2-A]PYRIMIDINES AS HIV VIRAL DNA INTEGRASE INHIBITORS

(75) Inventors: Jacques Banville, St-Hubert (CA); Roger Remillard, Napierville (CA); Serge Plamondon, Ste-Catherine (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 175 days.

(21) Appl. No.: 11/511,751

(22) Filed: Aug. 29, 2006

(65) Prior Publication Data

US 2007/0049606 A1 Mar. 1, 2007

Related U.S. Application Data

(60) Provisional application No. 60/713,080, filed on Aug. 31, 2005.

(51) Int. Cl.
| | |
|---|---|
| C07D 487/04 | (2006.01) |
| A61K 31/519 | (2006.01) |
| A61K 31/683 | (2006.01) |
| A61K 38/16 | (2006.01) |
| A61K 35/76 | (2006.01) |
| A61K 31/5513 | (2006.01) |
| A61K 31/662 | (2006.01) |
| A61K 31/52 | (2006.01) |
| A61K 31/522 | (2006.01) |
| A61K 31/655 | (2006.01) |
| A61K 31/497 | (2006.01) |
| A61K 31/536 | (2006.01) |
| A61K 31/568 | (2006.01) |
| C07F 9/32 | (2006.01) |
| A61P 31/18 | (2006.01) |
| C07D 243/04 | (2006.01) |

(52) U.S. Cl. .................. 514/81; 514/259.1; 514/221; 514/12; 514/220; 514/117; 514/263.4; 514/263.24; 514/151; 514/253.09; 514/230.5; 514/171; 544/281; 544/244; 540/568

(58) Field of Classification Search .................. 544/244, 544/281; 514/259.5, 81
See application file for complete search history.

(56) References Cited

U.S. PATENT DOCUMENTS

| | | |
|---|---|---|
| 2005/0256109 A1 | 11/2005 | Naidu |
| 2005/0261322 A1 | 11/2005 | Naidu |
| 2005/0267105 A1 | 12/2005 | Naidu |
| 2005/0267131 A1 | 12/2005 | Naidu |
| 2005/0267132 A1 | 12/2005 | Banville |
| 2006/0046985 A1 | 3/2006 | Crescenzi |

FOREIGN PATENT DOCUMENTS

| | | |
|---|---|---|
| EP | 1698628 | 9/2006 |
| JP | 2004 244320 | 2/2004 |
| WO | WO 2005/061490 | 7/2005 |
| WO | WO 2005/061501 | 7/2005 |
| WO | WO 2006/103399 | 10/2006 |

*Primary Examiner*—Brenda L Coleman
*Assistant Examiner*—Susanna Moore
(74) *Attorney, Agent, or Firm*—James Epperson

(57) ABSTRACT

The invention encompasses a series of bicyclic heterocyclic compounds of Formula I which are inhibitors of HIV integrase and prevent viral integration into human DNA. This action makes the compounds useful for treating HIV infection and AIDS. The invention also encompasses pharmaceutical compositions and methods for treating those infected with HIV.

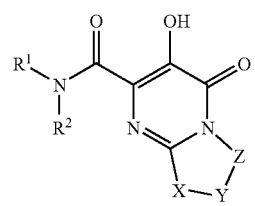

14 Claims, No Drawings

SUBSTITUTED IMIDAZO[1,2-A]PYRIMIDINES AS HIV VIRAL DNA INTEGRASE INHIBITORS

CROSS REFERENCE TO RELATED APPLICATIONS

This application claims the benefit of U.S. Provisional Application Ser. No. 60/713,080, filed Aug. 31, 2005.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfmavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/mL) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. *Science* 2000, 287, 646). And recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

DESCRIPTION OF THE INVENTION

The invention encompasses compounds of Formula I, including pharmaceutically acceptable salts, their pharmaceutical compositions, and methods for inhibiting HIV integrase and treating those infected with HIV.

One aspect of the invention is a compound of Formula I

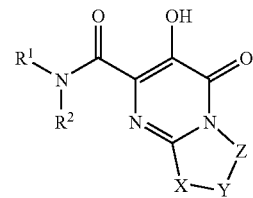

wherein:

$R^1$ is $(Ar^1)$alkyl;

$R^2$ is hydrogen, hydroxy, alkyl, or alkoxy;

$R^3$ is hydrogen, halo, hydroxy, cyano, alkyl, haloalkyl, alkoxy, haloalkoxy, $C_{4-6}$lactamyl, $N(R^6)SO_2R^7$, $N(R^6)COR^7$, $N(R^6)CO_2R^7$, $OCOR^7$, $OCO_2R^7$, $OCON(R^6)(R^6)$, $COR^7$, $CO_2R^6$, $CON(R^6)(R^6)$, $SOR^7$, $SO_2R^7$, $SO_2N(R^6)(R^6)$, $P(O)(OR^6)_2$, or $Ar^2$;

$R^4$ is hydrogen, halo, hydroxy, cyano, alkyl, alkoxy, haloalkyl, or haloalkoxy;

$R^5$ is hydrogen, halo, hydroxy, cyano, alkyl, alkoxy, haloalkyl, or haloalkoxy;

$R^6$ is hydrogen, alkyl, or cycloalkyl;

$R^7$ is alkyl or cycloalkyl;

$R^8$ is hydrogen or alkyl;

$R^9$ is hydrogen, alkyl, cycloalkyl, hydroxyalkyl, (alkoxy)alkyl, phenyl, or benzyl, wherein phenyl and benzyl are substituted with 0-2 substituents selected from the group consisting of halo, cyano, alkyl, alkoxy, halolkyl, and haloalkoxy;

$Ar^1$ is

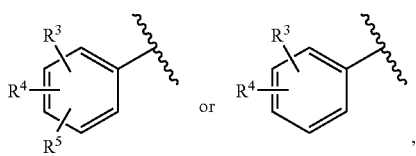

Ar² is tetrazolyl, triazolyl, pyrazolyl, imidazolyl, pyrrolyl, or dioxothiazinyl, and is substituted with 0-2 substituents selected from the group consisting of amino, oxo, halo, and alkyl; and X—Y-Z is N(R⁹)C(R⁸)₂C(R⁸)₂, N(R⁹)C(R⁸)₂C(R⁸)₂C(R⁸)₂, or N(R⁹)C(R⁸)₂C(R⁸)₂C(R⁸)₂C(R⁸)₂;

or a pharmaceutically acceptable salt thereof.

Another aspect of the invention is a compound of Formula I where R¹ is

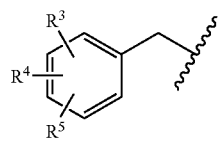

Another aspect of the invention is a compound of Formula I where R¹ is

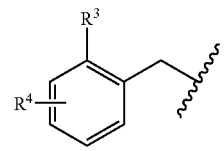

provided that R³ is not hydrogen.

Another aspect of the invention is a compound of Formula I 1 where R¹ is

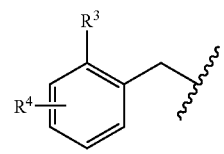

and R³ is C₄₋₆lactamyl, N(R⁶)SO₂R⁷, N(R⁶)COR⁷, N(R⁶)CO₂R⁷, OCOR⁷, OCO₂R⁷, OCON(R⁶)(R⁶), COR⁷, CO₂R⁶, CON(R⁶)(R⁶), SOR⁷, SO₂R⁷, SO₂N(R⁶)(R⁶), or Ar².

Another aspect of the invention is a compound of Formula I where R² is hydrogen.

Another aspect of the invention is a compound of Formula I where R³ is triazinyl substituted with 0-1 methyl groups; R⁴ is hydrogen, chloro, fluoro, or methyl; and R⁵ is hydrogen.

Another aspect of the invention is a compound of Formula I where R⁶ is hydrogen or alkyl.

Another aspect of the invention is a compound of Formula I where R⁷ is alkyl.

Another aspect of the invention is a compound of Formula I where R⁸ is hydrogen or methyl.

Another aspect of the invention is a compound of Formula I where X—Y-Z is N(R⁹)CH₂CH₂, N(R⁹)CH₂CH₂CH₂, or N(R⁹)CH₂CH₂CH₂CH₂.

Another aspect of the invention is a compound according to one of the following structures:

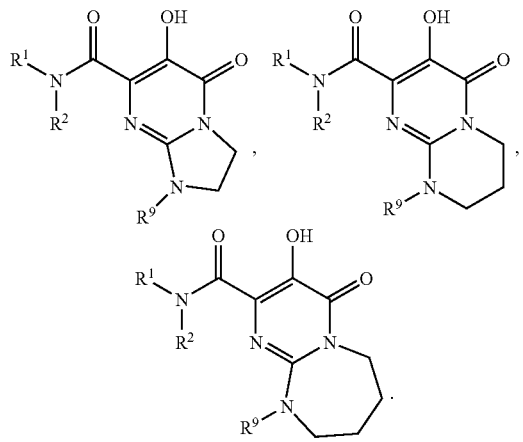

Another aspect of the invention is a compound according to the following structure

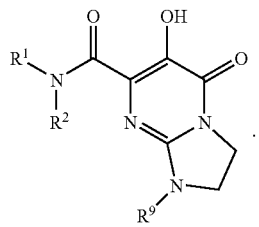

Another aspect of the invention is a compound of Formula I where R⁹ is alkyl, cycloalkyl, hydroxyalkyl (alkoxy)alkyl, phenyl, or benzyl.

For a compound of Formula I, any scope of R¹, R², R³, R⁴, R⁵, R⁶, R⁷, R⁸, R⁹, Ar¹, Ar², and X—Y-Z can be used independently with any scope of any other variable.

"C₄₋₆lactamyl" means a lactam of 4 to 6 carbons, for example caprolactam.

"Dioxothiazinyl" means

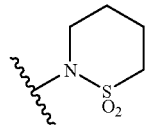

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art.

The invention includes all tautomeric forms of the compounds. An example of a tautomeric pair is shown below.

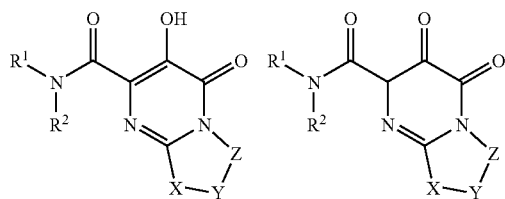

Synthetic Methods

The compounds of this invention can be made by various methods known in the art including those of the following schemes and in the specific embodiments section. The variables shown in the synthetic schemes are distinct from and should not be confused with the variables in the claims or the rest of the specification. The variables in the schemes are meant only to illustrate how to make some of the compounds of this invention.

Some formula I compounds can be synthesized from an appropriately substituted heterocycle I-1 according to Scheme I, where $R_a$ and P can serve as protecting groups (see Greene, T. W. and Wutz, P. G. M. *Protective Groups in Organic Synthesis*, Second Edition, 1991, John Wiley and Sons, New York). When P is benzyl or substituted benzyl it can be removed by hydrogenolysis ($H_2$—Pd/C) or acid hydrolysis (trifluoroacetic acid) to yield intermediate I-2. I-2 can be transaminated to I-4 by reaction with amine I-3. When $R_a$ is a lower alkyl group, $R_a$ can be removed under ester hydrolysis conditions, such as treatment with NaOH, LiOH, or KOH to deliver the corresponding carboxylic acid I-5. Alternatively, $R_a$ can be removed by nucleophilic displacement using NaI. When $R_a$ is benzyl and substituted benzyl, $R_a$ can be removed by hydrogenolysis. Intermediate I-5 can be coupled using amide bond forming reagents such as DCC, PyBOP, BOP or other reagents (see March, J. *Advanced Organic Chemistry*, Fourth Edition 1992 John Wiley & Sons, New York). The resulting intermediate I-6 can be deprotected as described for intermediate I-1.

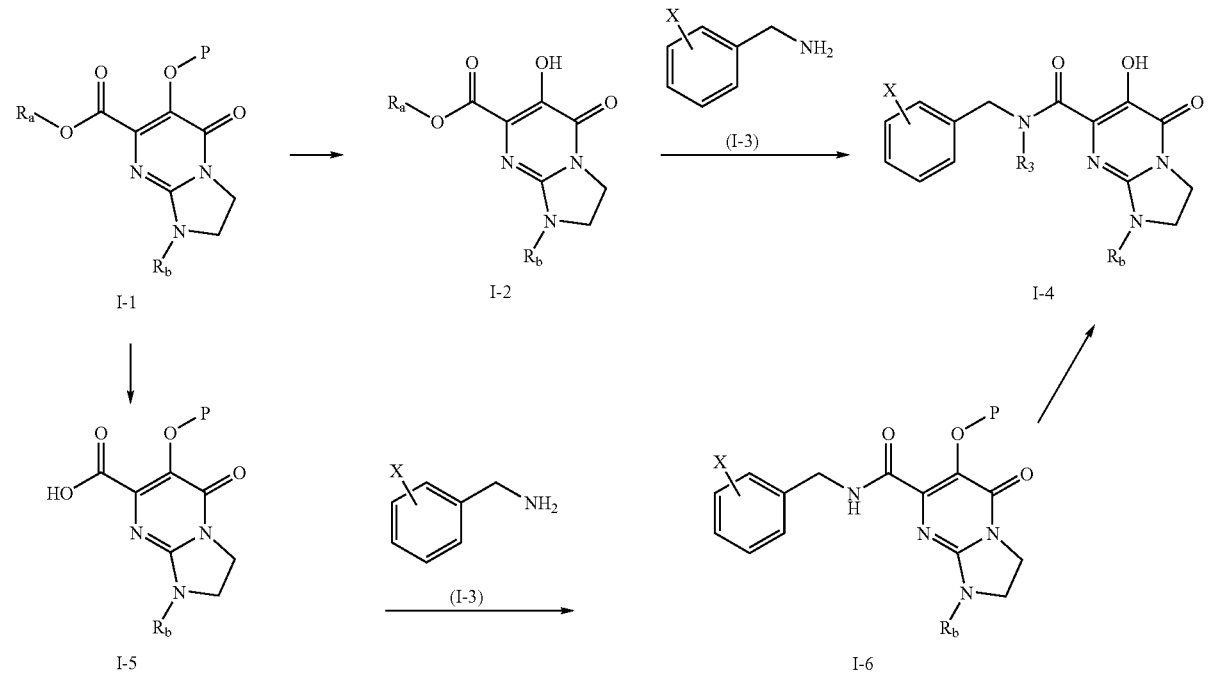

(P = protecting group)
$R_a$, $R_b$ = alkyl, aryl, benzyl

Some bicyclic heterocycles can be synthesized according to a variety of methods, some examples of which are illustrated in Scheme II. Using methods similar to that described in Sunderland, J. S.; Botta, M.; Aime, S.; Raymond, K. N. *Inorg. Chem.* 2001, 40, 6756-6756, II-1 and II-2 can be condensed to provide intermediate II-3. Intermediate II-3 can be reacted with thiourea to yield pyrimidinone II-4. Pyrimidinone II-4 can be transformed to II-5 by addition of an appropriately substituted ethylamine to the N-3 of the pyrimidinone. The sulfide of II-4 can be activated for nucleophilic displacement by treating with an appropriate oxidizing agent such as mCPBA to form the sulfone II-6. The sulfone can be displaced by the appropriately functionalized amino group to yield II-7. This compound can be carried on to the final product according to the methods described in Scheme I.

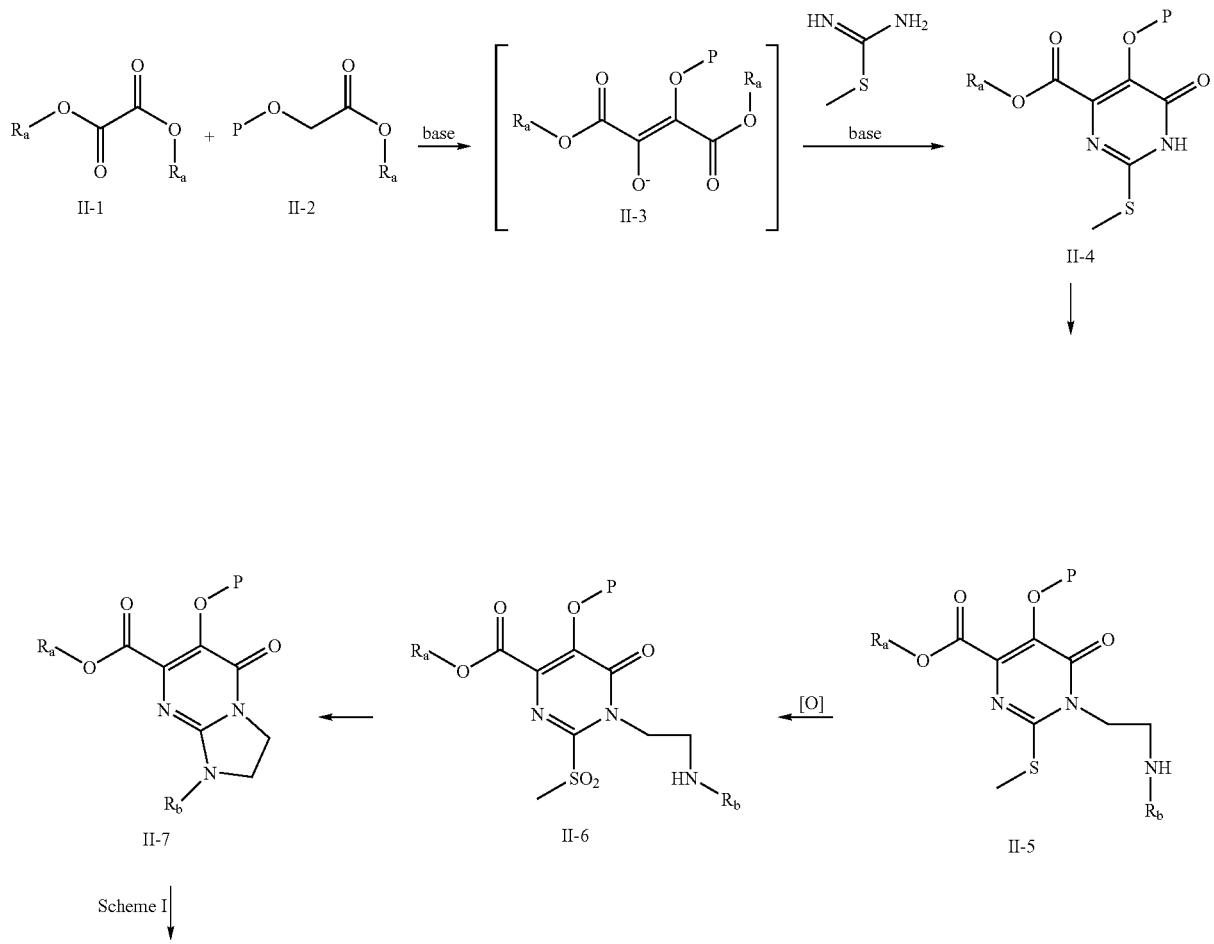

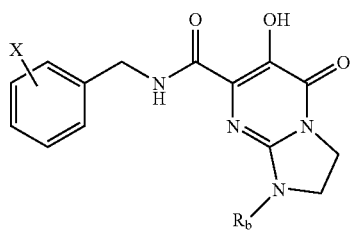

In Scheme III, the intermediate II-3 is prepared in the same manner as in Scheme II. Condensation with a cyclic guanidine, such as III-2 provides the bicyclic intermediate III-3, which in turn is carried on to final compound as described in Scheme I.

as a measure of integration. The reaction condition was as described in A. Engelman and R. Craigie, *J. Virol.* 69, 5908-5911 (1995). The sequences of substrate and target DNA were described in *Nucleic Acid Research* 22,1121-1122 (1994). Results shown in the Table 1. Activity equal to A refers to a compound having $IC_{50}=0.005$ to $0.010\ \mu M$ while B and C denote compounds having $IC_{50}=0.010$ to $0.030\ \mu M$ and $IC_{50}>0.030\ \mu M$ respectively.

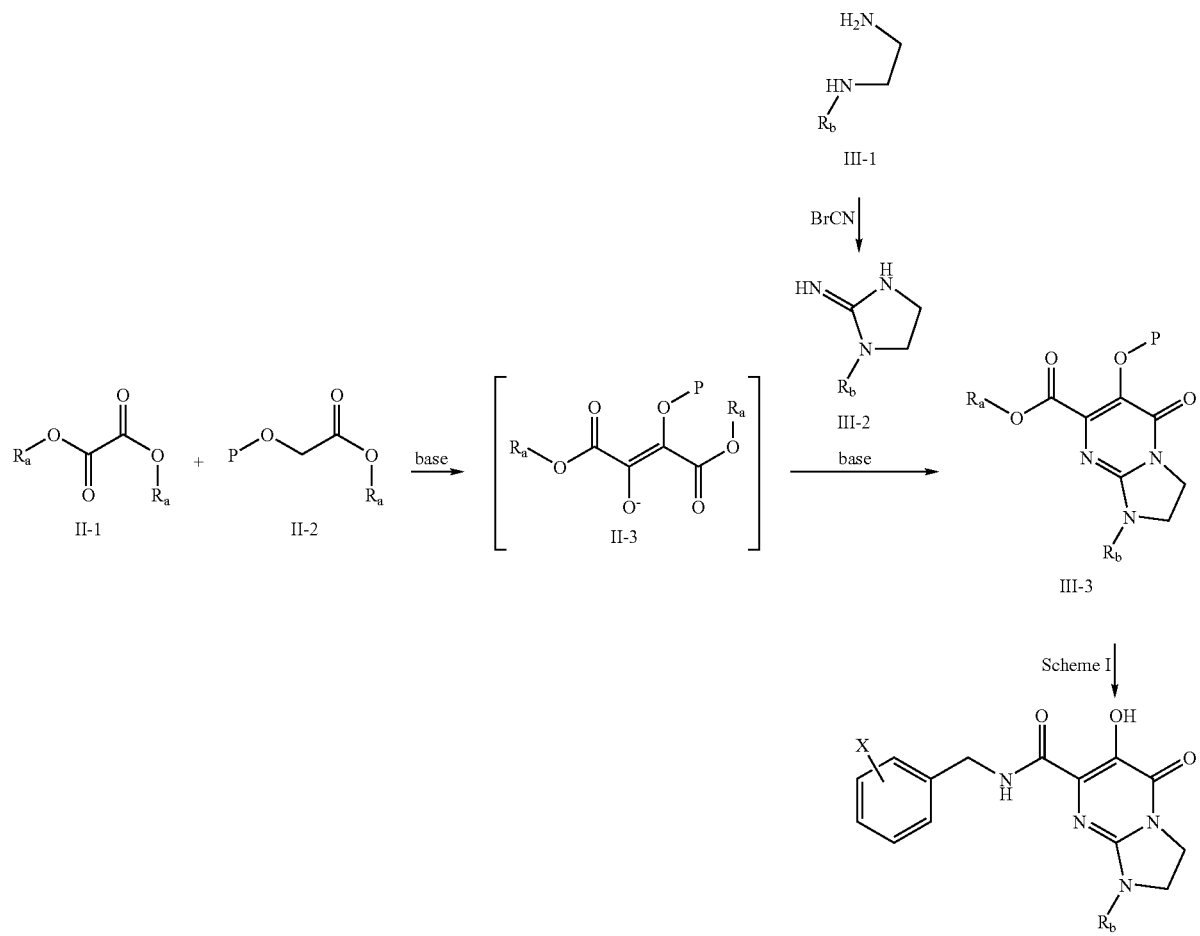

Scheme III.

Biological Methods

Another aspect of the invention is a method for inhibiting HIV integrase comprising contacting a compound of Formula I with HIV integrase.

Another aspect of the invention is a method for inhibiting HIV viral cDNA integration into human DNA comprising administering an effective amount of a compound of Formula I to a human cell infected with HIV.

HIV-Integrase Inhibition Activity. To evaluate in-vitro activity against HIV-integrase, 5 pmole of biotin labeled substrate DNA was bound to 100 µg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used

TABLE 1

| Example | Activity |
|---------|----------|
| 1 | B |
| 2 | B |
| 3 | B |
| 4 | B |
| 5 | B |
| 6 | B |
| 7 | B |
| 8 | A |
| 9 | B |
| 10 | C |
| 11 | A |
| 12 | B |
| 13 | B |
| 14 | B |
| 15 | A |

TABLE 1-continued

| Example | Activity |
|---|---|
| 16 | C |
| 17 | B |
| 18 | B |
| 19 | B |
| 20 | A |
| 21 | A |
| 22 | B |
| 23 | A |
| 24 | A |
| 25 | B |
| 26 | B |
| 27 | B |
| 28 | A |
| 29 | B |
| 30 | B |
| 31 | B |
| 32 | A |
| 33 | A |
| 34 | A |
| 35 | B |
| 36 | B |
| 37 | B |
| 38 | C |
| 39 | C |
| 40 | A |
| 41 | B |
| 42 | |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. *In Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $EC_{50}$=0.004 to 0.030 μM while B and C denote compounds with $EC_{50}$=0.030 to 0.1 μM and $EC_{50}$>0.1 μM respectively.

TABLE 2

| Example | Activity |
|---|---|
| 1 | C |
| 2 | C |
| 3 | C |
| 4 | C |
| 5 | C |
| 6 | C |
| 7 | C |
| 8 | C |
| 9 | A |

TABLE 2-continued

| Example | Activity |
|---|---|
| 10 | A |
| 11 | C |
| 12 | C |
| 13 | C |
| 14 | A |
| 15 | A |
| 16 | B |
| 17 | B |
| 18 | B |
| 19 | B |
| 20 | B |
| 21 | A |
| 22 | A |
| 23 | A |
| 24 | A |
| 25 | A |
| 26 | A |
| 27 | A |
| 28 | A |
| 29 | C |
| 30 | C |
| 31 | C |
| 32 | C |
| 33 | C |
| 34 | A |
| 35 | B |
| 36 | C |
| 37 | C |
| 38 | C |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut*. 2002, 27, 1101).

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is a method for treating HIV infection in a human patient comprising administering a therapeutically effective amount of a compound of Formula I, or a pharmaceutically acceptable salt thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition for treating HIV infection in a human patient comprising administering a therapeutically effective amount of a compound of Formula I, or a pharmaceutically acceptable salt thereof, with a pharmaceutically acceptable carrier.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred.

Some examples of dosages are 1 mg, 10 mg, 100 mg, 250 mg, 500 mg, and 1000 mg.

Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgment.

Table 3 lists some agents useful in treating AIDS and HIV infection which are suitable for this invention.

TABLE 3

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, |
| AL-721 | Ethigen (Los Angeles, CA) | PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |

TABLE 3-continued

| DRUG NAME | MANUFACTURER | INDICATION |
|---|---|---|
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |

TABLE 3-continued

| DRUG NAME | MANUFACTURER | INDICATION |
|---|---|---|
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |

TABLE 3-continued

| DRUG NAME | MANUFACTURER | INDICATION |
|---|---|---|
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

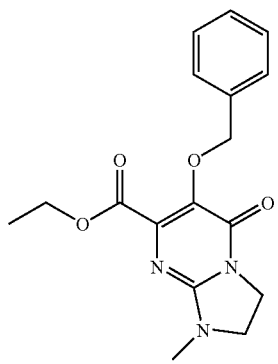

Intermediate 1

Ethyl 6-(benzyloxy)-1-methyl-5-oxo-1,2,3,5-tetrahydroimidazo[1,2-a]pyrimidine-7-carboxylate Diethyl oxalate (7.66 g, 52.4 mmol) and ethyl benzyloxyacetate (10.2 g, 52.5 mmol) in dry tetrahydrofuran (70 ml) were treated at 22° C. with sodium hydride (2.31 g of a 60% dispersion in mineral oil, 57.7 mmol). Ethanol (40 μl) was then added and the mixture was stirred under argon for 16 h. The tetrahydrofuran was then concentrated under reduced pressure and the residue was treated with a mixture of 1-methyl-4,5-dihydro-1H-imidazol-2-amine hydrobromide (9.45 g, 52.5 mmol) (J. V. Grennhill et al. J. Chem. Soc. Perkin Trans.II, 1985, 1255-1264) in a solution of sodium ethoxide (26.0 mmol, prepared from 0.60 g of sodium) in ethanol (70 ml) and the resulting mixture was heated at 60° C. for 3 h. Acetic acid (2 ml) was added and the ethanol was evaporated under reduced pressure. The residue was diluted with ethyl acetate washed successively with saturated sodium bicarbonate and brine, dried over anhydrous magnesium sulfate and concentrated under reduced pressure. Chromatography on silica gel (elution gradient of ethanol 0-20% in ethyl acetate) gave 5.33 g (30% yield) of intermediate 1 as white crystals; mp 135-137° C. (ethyl acetate). $^1$HNMR 400 MHz (CDCl$_3$) δ (ppm): 1.32 (3H, t, J=7.1 Hz, CH$_3$), 3.03 (3H, s, NCH$_3$), 3.71 (2H, t, J=9.1 Hz, CH$_2$), 4.15 (2H, t, J=9.1 Hz, CH$_2$), 4.33 (2H, q, J=7.1 Hz, OCH$_2$), 5.10 (2H, s, OCH$_2$), 7.3-7.51 (5H, m, aromatics). Anal. Calcd for C$_{17}$H$_{19}$N$_3$O$_4$: C, 61.99, H 5.81; N, 12.75. Found: C, 61.73; H, 5.78; N, 12.73.

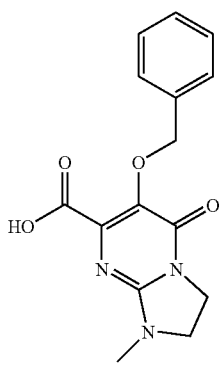

Intermediate 2

6-(Benzyloxy)-1-methyl-5-oxo-1,2,3,5-tetrahydroimidazo[1,2-a]pyrimidine-7-carboxylic Acid A solution of ethyl 6-(benzyloxy)-1-methyl-5-oxo-1,2,3,5-tetrahydroimidazo[1,2-a]pyrimidine-7-carboxylate (0.971 g, 2.95 mmol) in a mixture tetrahydrofuran (20 ml) and ethanol (20 ml) was treated with 15 ml of 1 N sodium hydroxide and the mixture was stirred at 40° C. for 30 min. The solvent was then concentrated under reduced pressure and the residue was acidified with 1 N hydrochloric acid (20 ml). The precipitate formed was filtered, washed with water and dried in vacuo to give 0.874 g (98% yield) of the title acid as a white solid; mp 203° C. (dec; ethyl acetate). $^1$HNMR 400 MHz (DMSO-d$_6$) δ (ppm): 2.87 (3H, s, NCH$_3$), 3.66 (2H, t, J=9 Hz, CH$_2$), 4.01 (2H, t, J=9 Hz, CH$_2$), 4.91 (2H, s, OCH$_2$), 7.3-7.45 (5H, m, aromatics). HRMS (ESI$^+$) calculated for C$_{15}$H$_{16}$N$_3$O$_4$ [M+H$^+$]: 302.1141. found: 302.1127.

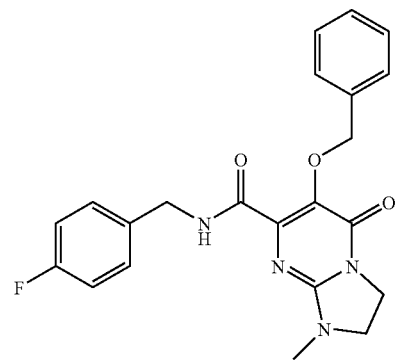

Intermediate 3

N-(4-Fluorobenzyl)-6-(benzyloxy)-1-methyl-5-oxo-1,2,3,5-tetrahydroimidazo[1,2-a]pyrimidine-7-carboxamide A mixture of 6-(benzyloxy)-1-methyl-5-oxo-1,2,3,5-tetrahydroimidazo[1,2-a]pyrimidine-7-carboxylic acid (0.393 g, 1.30 mmol) and 4-fluorobenzylamine (0.163 g, 1.30 mmol) in acetonitrile (15 ml) was treated at 25° C. with triethylamine (0.42 ml, 2.5 mmol) followed by benzotriazole-1-yl-oxy-tris-(dimethylamino)-phosphoniumhexafluorophosphate (0.662 g, 1.49 mmol). After 3 h, the reaction mixture was diluted with ethyl acetate, washed successively with 0.1 N hydrochloric acid, saturated sodium bicarbonate and brine, dried over anhydrous magnesium sulfate and concentrated under reduced pressure. Crystallization of the residual solid from ethyl acetate gave 0.407 g (76% yield) of the title amide as white cubes; mp 189-191° C. $^1$HNMR 400 MHz (CDCl$_3$) δ (ppm): 3.02 (3H, s, NCH$_3$), 3.70 (2H, t, J=9 Hz, CH$_2$), 4.15 (2H, t, J=9 Hz, CH$_2$), 4.50 (2H, d, J=5.6 Hz, NCH$_2$), 5.11 (2H, s, OCH$_2$), 7.0 (2H, m, aromatics), 7.24 (2H, m, aromatics), 7.3-7.45 (5H, m, aromatics), 7.71 (1H, broad t, NH). Anal. Calcd for $C_{22}H_{21}FN_4O_3$: C, 64.69; H, 5.18; N, 13.71. Found: C, 64.41; H, 5.10; N, 13.72.

EXAMPLE 1

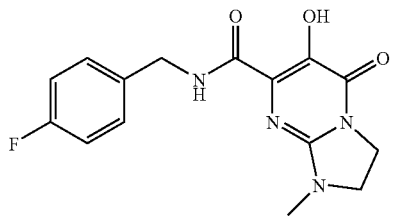

N-(4Fluorobenzyl)-6-hydroxy-1-methyl-5-oxo-1,2,3,5-tetrahydroimidazo[1,2-a]pyrimidine-7-carboxamide A solution of N-(4-fluorobenzyl)-6-(benzyloxy)-1-methyl-5-oxo-1,2,3,5-tetrahydroimidazo[1,2-a]pyrimidine-7-carboxamide (0.202 g, 0.495 mmol) in a mixture of ethyl acetate (150 ml) and ethanol (20 ml) at 25° C. was hydrogenated over 10% palladium on activated carbon (50 mg) and under one atmosphere of hydrogen for one hour to give 0.130 g (83% yield) of the title compound as white needles; mp 212° C. (ethyl acetate). $^1$HNMR 400 MHz (CDCl$_3$) δ (ppm): 2.93 (3H, s, CH$_3$), 3.63 (2H, t, J=8.6 Hz, CH$_2$), 4.14 (2H, t, J=8.6 Hz, CH$_2$), 4.59 (2H, d, J=6.0 Hz, NCH$_2$), 7.07 (2H, m, aromatics), 7.33 (2H, m, aromatics), 7.89 (1H, broad t, NH), 11.57 (1H, s, OH). HRMS (ESI$^+$) calculated for $C_{15}H_{16}FN_4O_3$ [M+H$^+$]: 319.1206. found: 319.1191.

Intermediate 4

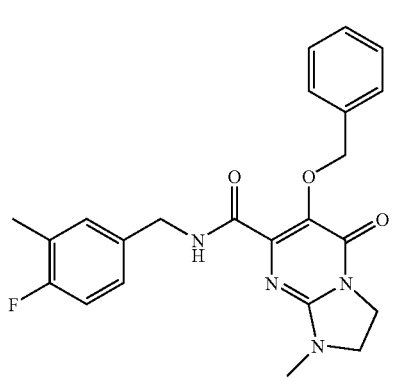

N-(4-Fluoro-3-methylbenzyl)-6-(benzyloxy)-1-methyl-5-oxo-1,2,3,5-tetrahydroimidazo[1,2-a]pyrimidine-7-carboxamide Coupling of 6-(benzyloxy)-1-methyl-5-oxo-1,2,3,5-tetrahydroimidazo[1,2-a]pyrimidine-7-carboxylic acid (0.439 g, 1.46 mmol) and 4-fluoro-3-methylbenzylamine (0.203 g, 1.46 mmol) as described for the synthesis of intermediate 3 gave 0.372 g (60% yield) of the title amide as white crystals; mp 182-184° C. (ethyl acetate). $^1$HNMR 400 MHz (DMSO-d$_6$) δ (ppm): 2.12 (3H, s, CH$_3$), 2.90 (3H, s, NCH$_3$), 3.66 (2H, t, J=8.6 Hz, CH$_2$), 4.02 (2H, t, J=8.6 Hz, CH$_2$), 4.33 (2H, d, J=6.0 Hz, NCH$_2$), 4.88 (2H, s, OCH$_2$), 6.97 (1H, m, aromatic), 7.11-7.2 (2H, m, aromatics), 7.3-7.4 (5H, m, aromatics), 8.81 (1H, broad t, NH). HRMS (ESI$^+$) calculated for $C_{23}H_{24}FN_4O_3$ [M+H$^+$]: 423.1832. found: 423.1827.

EXAMPLE 2

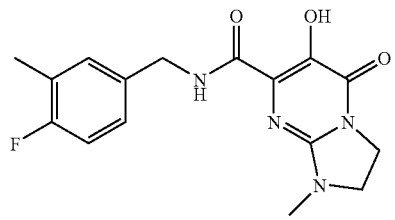

N-(4-Fluoro-3-methylbenzyl)-6-hydroxy-1-methyl-5-oxo-1,2,3,5-tetrahydroimidazo[1,2-a]pyrimidine-7-carboxamide Hydrogenolysis of N-(4-fluoro-3-methylbenzyl)-6-(benzyloxy)-1-methyl-5-oxo-1,2,3,5-tetrahydroimidazo[1,2-a]pyrimidine-7-carboxamide (0.338 g, 0.80 mmol) as described for example 1 gave 0.191 g (72% yield) of the title compound as white crystals; mp 187-189° C. (ethyl acetate). $^1$HNMR 400 MHz (CDCl$_3$) δ (ppm): 2.30 (3H, s, CH$_3$), 2.93 (3H, s, CH$_3$), 3.63 (2H, t, J=8.6 Hz, CH$_2$), 4.14 (2H, t, J=8.6 Hz, CH$_2$), 4.54 (2H, d, J=6.2 Hz, NCH$_2$), 7.0 (1H, m, aromatic), 7.12-7.18 (2H, m, aromatics), 7.87 (1H, broad t, NH), 11.59 (1H, s, OH). Anal. Calcd for $C_{16}H_{17}FN_4O_3$: C, 57.82; H, 5.15; N, 16.85. Found: C, 57.51; H, 5.27; N, 16.69.

Intermediate 5

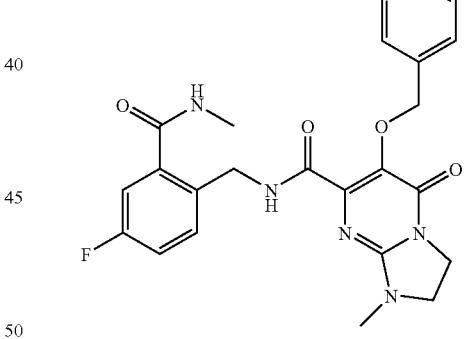

N-(4-Fluoro-2-(methylcarbamoyl)benzyl)-6-(benzyloxy)-1-methyl-5-oxo-1,2,3,5-tetrahydroimidazo[1,2-a]pyrimidine-7-carboxamide Coupling of 6-(benzyloxy)-1-methyl-5-oxo-1,2,3,5-tetrahydroimidazo[1,2-a]pyrimidine-7-carboxylic acid (0.300 g, 1.0 mmol) and 2-(aminomethyl)-5-fluoro-N-methylbenzamide trifluoroacetate salt (0.295 g, 1.0 mmol) as described for the synthesis of intermediate 3 gave 0.253 g (54% yield) of the title amide as white crystals; mp 184° C. (ethyl acetate-hexane). $^1$HNMR 400 MHz (DMSO-d$_6$) δ (ppm): 2.78 (3H, d, J=4.5 Hz, NCH$_3$), 2.91 (3H, s, NCH$_3$), 3.66 (2H, t, J=8.9 Hz, CH$_2$), 4.02 (2H, t, J=8.9 Hz, CH$_2$), 4.46 (2H, d, J=6.2 Hz, NCH$_2$), 4.90 (2H, s, OCH$_2$), 7.04 (1H, m, aromatic), 7.25 (1H, dd, J=2.6 Hz and J=9.1 Hz, aromatic), 7.29-7.46 (6H, m,

EXAMPLE 3

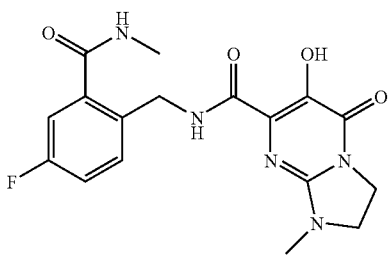

N-(4-Fluoro-2-(methylcarbamoyl)benzyl)-6-hydroxy-1-methyl-5-oxo-1,2,3,5-tetrahydroimidazo[1,2-a]pyrimidine-7-carboxamide Hydrogenolysis of N-(4-fluoro-2-(methylcarbamoyl)benzyl)-6-(benzyloxy)-1-methyl-5-oxo-1,2,3,5-tetrahydroimidazo[1,2-a]pyrimidine-7-carboxamide (0.223 g, 0.48 mmol) as described for example 1 gave 0.048 g (27% yield) of the title compound a white solid. $^1$HNMR 400 MHz (CDCl$_3$) δ (ppm): $^1$HNMR 400 MHz (DMSO-d$_6$) δ (ppm): 2.80 (3H, d, J=4.5 Hz, CH$_3$), 2.89 (3H, s, NCH$_3$), 3.56 (2H, t, J=8.6 Hz, CH$_2$), 3.97 (2H, t, J=8.6 Hz, CH$_2$), 4.53 (2H, d, J=6.5 Hz, NCH$_2$), 7.27-7.4 (3H, m, aromatics), 8.54 (1H, broad q, NH), 9.18 (1H, broad t, NH), 11.60 (1H, s, OH). HRMS (ESI$^+$) calculated for C$_{17}$H$_{19}$FN$_5$O$_4$ [M+H$^+$]: 376.1421. found: 376.1410.

Intermediate 6

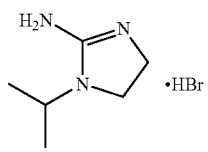

1-Isopropyl-4,5-dihydro-1H-imidazol-2-amine hydrobromide

A solution of N-isopropylethylenediamine (10.0 g, 0.097 mol) in methanol (10 ml) was cooled to 0° C. and treated dropwise with a solution of cyanogen bromide (10.37 g, 0.098 mol) in methanol (25 ml) while maintaining the temperature below 10° C. The reaction mixture was then heated to 80° C. for 45 min, cooled and concentrated under reduced pressure. Crystallization of the residue from cold ethanol gave 10.4 g (50% yield) of the title product as white crystals; mp 154-155° C. $^1$HNMR 400 MHz (CDCl$_3$) δ (ppm): 1.27 (6H, d, J=6.6 Hz, 2×CH$_3$), 3.57-3.75 (4H, m, 2×CH$_2$), 4.41 (1H, m, CH).

Intermediate 7

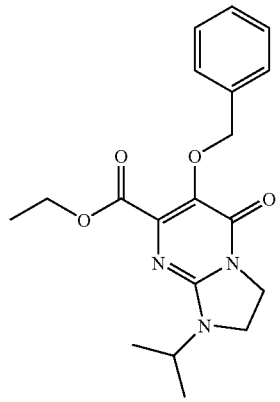

Ethyl 6-(benzyloxy)-1-isopropyl-5-oxo-1,2,3,5-tetrahydroimidazo[1,2-a]pyrimidine-7-carboxylate Reaction of the adduct of diethyl oxalate (7.26 g, 49.7 mmol), ethyl benzyloxyacetate (9.65 g, 49.7 mmol) and sodium hydride (2.19 g of a 60% dispersion in mineral oil, 54.7 mmol) with 1-isopropyl-4,5-dihydro-1H-imidazol-2-amine hydrobromide (10.33 g, 49.7 mmol) as described for intermediate 1 gave 6.79 g (38% yield) of the title ester as white crystals; mp 131-132° C. (ethyl acetate). $^1$HNMR 400 MHz (CDCl$_3$) δ (ppm): 1.22 (6H, d, J=6.8 Hz, 2×CH$_3$), 1.31 (3H, t, J=7.1 Hz, CH$_3$), 3.66 (2H, t, J=9 Hz, CH$_2$), 4.13 (2H, t, J=9 Hz, CH$_2$), 4.31 (2H, q, J=7.1 Hz, OCH$_2$), 4.40 (1H, m, CH), 5.08 (2H, s, OCH$_2$), 7.3-7.39 (3H, m, aromatics), 7.49 (2H, m, aromatics). Anal. Calcd for C$_{19}$H$_{23}$N$_3$O$_4$: C, 63.85; H, 6.48, N 11.75. Found: C, 63.57; H, 6.76; N, 11.98.

Intermediate 8

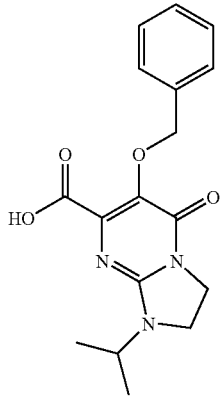

6-(Benzyloxy)-1-isopropyl-5-oxo-1,2,3,5-tetrahydroimidazo[1,2-a]pyrimidine-7-carboxylic acid Saponification of ethyl 6-(benzyloxy)-1-isopropyl-5-oxo-1,2,3,5-tetrahydroimidazo[1,2-a]pyrimidine-7-carboxylate (2.00 g, 5.60 mmol) as described for intermediate 2 gave 1.84 g (100% yield) of the title acid as a white solid; mp 163-165° C. (ethyl acetate). $^1$HNMR 400 MHz (CDCl$_3$) δ (ppm): 1.23 (6H, d, J=6.7 Hz, 2×CH$_3$), 3.67 (2H, t, J=9 Hz, CH$_2$), 4.14 (2H, t, J=9 Hz, CH$_2$), 4.34 (1H, m, CH), 5.23 (2H, s, OCH$_2$), 7.3-7.39 (3H, m, aromatics), 7.57 (2H, m, aromatics). HRMS (ESI$^+$) calculated for $C_{17}H_{20}N_3O_4$ [M+H$^+$]: 330.1454. found: 330.1458.

t, J=8.6 Hz, CH$_2$), 4.22 (1H, m, CH), 4.59 (2H, d, J=6.3 Hz, NCH$_2$), 7.07 (2H, m, aromatics), 7.33 (2H, m, aromatics), 7.88 (1H, broad t, NH), 11.51 (1H, broad, OH). HRMS (ESI$^+$) calculated for $C_{17}H_{20}FN_4O_3$ [M+H$^+$]: 347.1519. found: 347.1520.

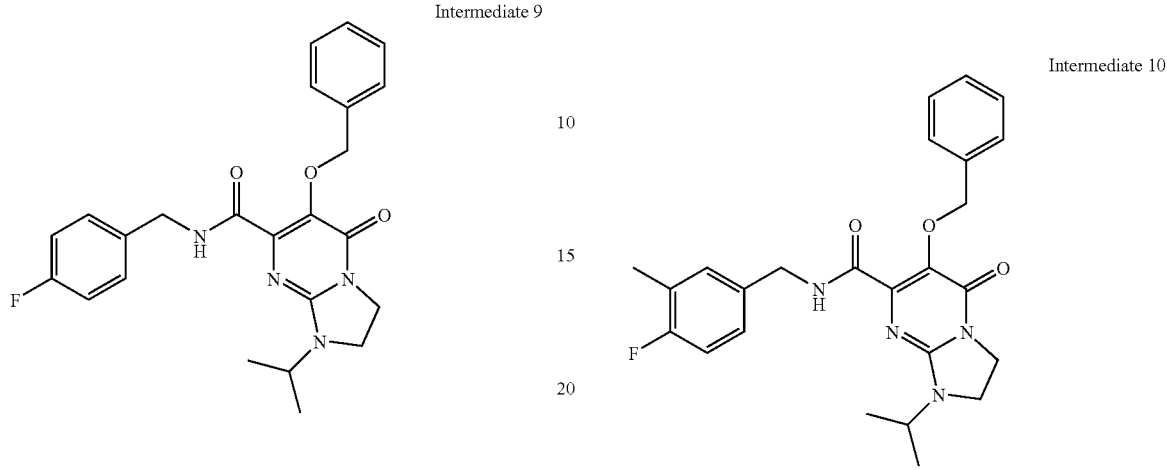

Intermediate 9

N-(4-Fluorobenzyl)-6-(benzyloxy)-1-isopropyl-5-oxo-1,2,3,5-tetrahydroimidazo[1,2-a]pyrimidine-7-carboxamide Coupling of 6-(benzyloxy)-1-isopropyl-5-oxo-1,2,3,5-tetrahydroimidazo[1,2-a]pyrimidine-7-carboxylic acid (0.300 g, 0.91 mmol) and 4-fluorobenzylamine (0.120 g, 0.96 mmol) as described for the synthesis of intermediate 3 gave 0.385 g (96% yield) of the title amide as white crystals; mp 166-167° C. (ethyl acetate). $^1$HNMR 400 MHz (CDCl$_3$) δ (ppm): 1.23 (6H, d, J=6.8 Hz, 2×CH$_3$), 3.67 (2H, t, J=9 Hz, CH$_2$), 4.14 (2H, t, J=9 Hz, CH$_2$), 4.42 (1H, m, CH), 4.50 (2H, d, J=6.0 Hz, NCH$_2$), 5.09 (2H, s, OCH$_2$), 7.0 (2H, m, aromatics), 7.25 (2H, m, aromatics), 7.3-7.37 (3H, m, aromatics), 7.46 (2H, m, aromatics), 7.69 (1H, broad t, NH). Anal. Calcd for $C_{24}H_{25}FN_4O_3$: C, 66.04; H, 5.77, N 12.83. Found: C, 65.84; H, 5.85; N, 12.58.

Intermediate 10

N-(4-Fluoro-3-methylbenzyl)-6-(benzyloxy)-1-isopropyl-5-oxo-1,2,3,5-tetrahydroimidazo[1,2-a]pyrimidine-7-carboxamide Coupling of 6-(benzyloxy) 1-isopropyl-5-oxo-1,2,3,5-tetrahydroimidazo[1,2-a]pyrimidine-7-carboxylic acid (0.300 g, 0.91 mmol) and 4-fluoro-3-methylbenzylamine (0.133 g, 0.95 mmol) as described for the synthesis of intermediate 3 gave 0.384 g (93% yield) of the title amide as white crystals (ethyl acetate-hexane). $^1$HNMR 400 MHz (CDCl$_3$) δ (ppm): 1.23 (6H, d, J=6.6 Hz, 2×CH$_3$), 2.25 (3H, broad d, J=1.8 Hz, CH$_3$), 3.67 (2H, t, J=9 Hz, CH$_2$), 4.13 (2H, t, J=9 Hz, CH$_2$), 4.41 (1H, m, CH), 4.46 (2H, d, J=5.8 Hz, NCH$_2$), 5.08 (2H, s, OCH$_2$), 6.94 (1H, m, aromatic), 7.04-7.08 (1H, m, aromatic), 7.11 (1H, m, aromatic), 7.3-7.36 (3H, m, aromatics), 7.42-7.46 (2H, m, aromatics), 7.69 (1H, broad t, NH). HRMS (ESI$^+$) calculated for $C_{25}H_{28}FN_4O_3$ [M+H$^+$]: 451.2145. found: 451.2141.

EXAMPLE 4

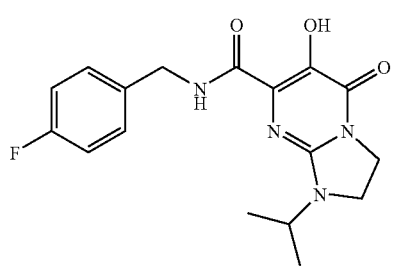

N-(4-Fluorobenzyl)-6-hydroxy-1-isopropyl-5-oxo-1,2,3,5-tetrahydroimidazo[1,2-a]pyrimidine-7-carboxamide Hydrogenolysis of N-(4-fluorobenzyl)-6-(benzyloxy)-1-isopropyl-5-oxo-1,2,3,5-tetrahydroimidazo[1,2-a]pyrimidine-7-carboxamide (0.200 g, 0.46 mmol) as described for example 1 gave 0.134 g (84% yield) of the title compound as a white solid. $^1$HNMR 400 MHz (CDCl$_3$) δ (ppm): 1.21 (6H, d, J=6.8 Hz, 2×CH$_3$), 3.60 (2H, t, J=8.6 Hz, CH$_2$), 4.13 (2H,

EXAMPLE 5

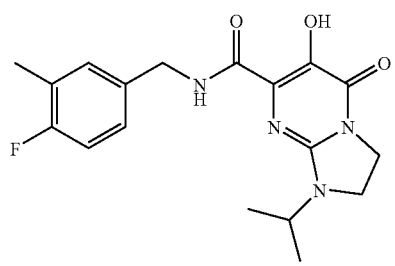

N-(4-Fluoro-3-methylbenzyl)-6-hydroxy-1-isopropyl-5-oxo-1,2,3,5-tetrahydroimidazo[1,2-a]pyrimidine-7-carboxamide Hydrogenolysis of N-(4-fluoro-3-methylbenzyl)-6-(benzyloxy)-1-isopropyl-5-oxo-1,2,3,5-tetrahydroimidazo[1,2-a]pyrimidine-7-carboxamide (0.200 g, 0.44 mmol) as described for example 1 gave 0.130 g (81% yield) of the title compound a white solid. $^1$HNMR 400 MHz (CDCl$_3$) δ (ppm): 1.21 (6H, d, J=6.8 Hz, 2×CH$_3$), 2.29 (3H, d, J=1.7 Hz, CH$_3$), 3.60 (2H, t, J=8.5 Hz, CH$_2$), 4.13 (2H, t, J=8.5 Hz, CH$_2$), 4.22 (1H, m, CH), 4.55 (2H, d, J=6.4 Hz, NCH$_2$), 7.0 (1H, m, aromatic), 7.15 (2H, m, aromatics), 7.86 (1H, broad t, NH), 11.54 (1H, broad, OH). HRMS (ESI$^+$) calculated for C$_{18}$H$_{22}$FN$_4$O$_3$ [M+H$^+$]: 361.1676. found: 361.1691.

Intermediate 11

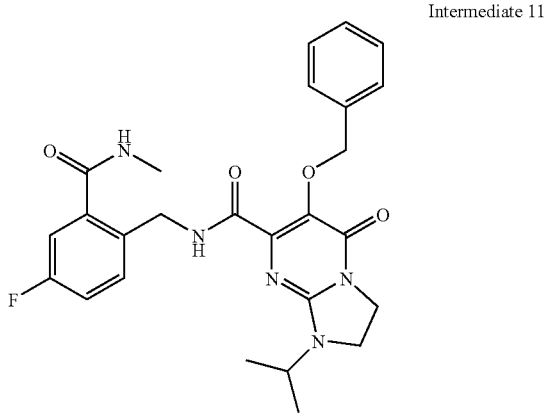

N-(4-Fluoro-2-(methylcarbamoyl)benzyl)-6-(benzyloxy)-1-isopropyl-5-oxo-1,2,3,5-tetrahydroimidazo[1,2-a]pyrimidine-7-carboxamide Coupling of 6-(benzyloxy)-1-isopropyl-5-oxo-1,2,3,5-tetrahydroimidazo[1,2-a]pyrimidine-7-carboxylic acid (0.300 g, 0.91 mmol) and 2-(aminomethyl)-5-fluoro-N-methylbenzamide trifluoroacetate salt (0.210 g, 0.96 mmol) as described for the synthesis of intermediate 3 gave 0.328 g (72% yield) of the title amide as white crystals; mp 197-198° C. (ethyl acetate). $^1$HNMR 400 MHz (CDCl$_3$) δ (ppm): 1.23 (6H, d, J=6.8 Hz, 2×CH$_3$), 2.98 (3H, d, J=5 Hz, NCH$_3$), 3.66 (2H, t, J=9 Hz, CH$_2$), 4.12 (2H, t, J=9 Hz, CH$_2$), 4.43 (1H, m, CH), 4.48 (2H, d, J=6.3 Hz, NCH$_2$), 5.09 (2H, s, OCH$_2$), 7.05 (1H, m, aromatic), 7.13-7.17 (2H, m, aromatics), 7.3-7.35 (4H, m, NH and aromatics), 7.43-7.46 (2H, m, aromatics), 8.35 (1H, broad t, NH). Anal. Calcd for C$_{26}$H$_{28}$FN$_5$O$_4$: C, 63.27; H, 5.71; N, 14.19. Found: C, 63.06; H, 5.65; N, 14.02.

EXAMPLE 6

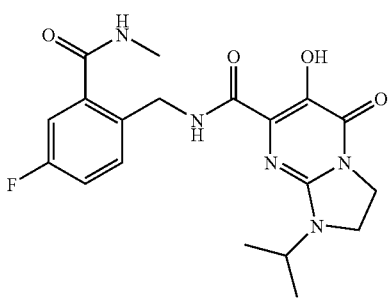

N-(4-Fluoro-2-(methylcarbamoyl)benzyl)-6-hydroxy-1-isopropyl-5-oxo-1,2,3,5-tetrahydroimidazo[1,2-a]pyrimidine-7-carboxamide Hydrogenolysis of N-(4-Fluoro-2-(methylcarbamoyl)benzyl)-6-(benzyloxy)-1-isopropyl-5-oxo-1,2,3,5-tetrahydroimidazo[1,2-a]pyrimidine-7-carboxamide (0.200 g, 0.40 mmol) as described for example 1 gave 0.125 g (77% yield) of the title compound white crystals; mp 205° C. (dec) (dichloromethane-ethyl acetate). $^1$HNMR 400 MHz (CDCl$_3$) δ (ppm): 1.24 (6H, d, J=6.6 Hz, 2×CH$_3$), 3.04 (3H, d, J=5.0 Hz, NCH$_3$), 3.59 (2H, t, J=8.5 Hz, CH$_2$), 4.09 (2H, t, J=8.5 Hz, CH$_2$), 4.31 (1H, m, CH), 4.61 (2H, d, J=6.6 Hz, NCH$_2$), 6.42 (1H, broad, NH), 7.10-7.20 (2H, m, aromatics), 7.49 (1H, dd, J=5.5 Hz and J=8.5 Hz, aromatic), 8.65 (1H, broad t, NH), 11.45 (1H, broad, OH). Anal. Calcd for C$_{19}$H$_{22}$FN$_5$O$_4$: C, 56.57; H, 5.49; N, 17.36. Found: C 56.34; H, 5.24; N, 17.26.

Intermediate 12

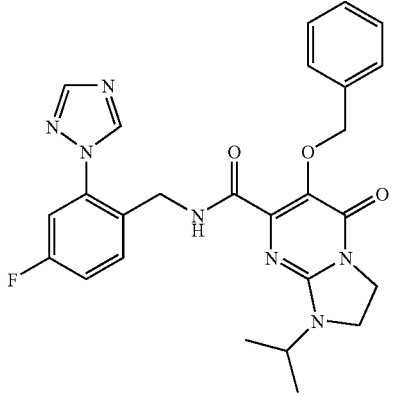

N-(4-Fluoro-2-(1H-1,2,4-triazol-1-yl)benzyl)-6-(benzyloxy)-1-isopropyl-5-oxo-1,2,3,5-tetrahydroimidazo[1,2-a]pyrimidine-7-carboxamide Coupling of 6-(benzyloxy)-1-isopropyl-5-oxo-1,2,3,5-tetrahydroimidazo[1,2-a]pyrimidine-7-carboxylic acid (0.300 g, 0.91 mmol) and (4-fluoro-2-(1H-1,2,4-triazol-1-yl)phenyl)methanamine hydrochloride (0.210 g, 0.96 mmol) as described for the synthesis of intermediate 3 gave 0.349 g (76% yield) of the title amide as white crystals; mp 171-172° C. (ethyl acetate). $^1$HNMR 400 MHz (CDCl$_3$) δ (ppm): 1.24 (6H, d, J=6.8 Hz, 2×CH$_3$), 3.66 (2H, t, J=9 Hz, CH$_2$), 4.13 (2H, t, J=9 Hz, CH$_2$), 4.41 (2H, d, J=6.3 Hz, NCH$_2$), 4.43 (1H, m, CH), 5.10 (2H, s, OCH$_2$), 7.06 (1H, dd, J=2.6 Hz and J=8.6 Hz, aromatic), 7.17 (1H, m, aromatic), 7.29-7.31 (3H, m, aromatics), 7.45-7.48 (2H, m, aromatics), 7.71 (1H, dd, J=5.9 Hz and J=8.6 Hz, aromatic), 8.0 (1H, s, CH), 8.36 (1H, broad t, NH), 8.39 (1H, s, CH). Anal. Calcd for C$_{26}$H$_{26}$FN$_7$O$_3$: C, 62.01; H, 5.20; N, 19.47. Found: C, 62.00; H, 5.20; N, 19.50.

EXAMPLE 7

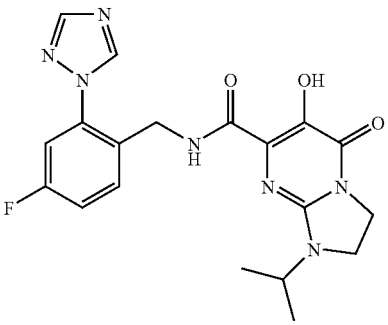

N-(4-Fluoro-2-(1H-1,2,4-triazol-1-yl)benzyl)-6-hydroxy-1-isopropyl-5-oxo-1,2,3,5-tetrahydroimidazo[1,2-a]pyrimidine-7-carboxamide Hydrogenolysis of N-(4-fluoro-2-(1H-1,2,4-triazol-1-yl)benzyl)-6-(benzyloxy)-1-isopropyl-5-oxo-1,2,3,5-tetrahydroimidazo[1,2-a]pyrimidine-7-carboxamide (0.200 g, 0.40 mmol) as described for example 1 gave 0.134 g (82% yield) of the title compound white crystals (ethyl acetate). $^1$HNMR 400 MHz (CDCl$_3$) δ (ppm): 1.27 (6H, d, J=6.5 Hz, 2×CH$_3$), 3.60 (2H, t, J=8.5 Hz, CH$_2$), 4.12 (2H, t, J=8.5 Hz, CH$_2$), 4.25 (1H, m, CH), 4.48 (2H, d, J=6.8 Hz, NCH$_2$), 7.13 (1H, dd, J=2.5 Hz and J=8.4 Hz, aromatic), 7.24 (1H, m, aromatic), 7.69 (1H, dd, J=5.8 Hz and J=8.6 Hz, aromatic), 8.18 (1H, s, CH), 8.46 (1H, s, CH), 8.66 (1H, broad t, NH), 11.41 (1H, broad, OH). HRMS (ESI$^+$) calculated for C$_{19}$H$_{21}$FN$_7$O$_3$ [M+H$^+$]: 414.1690. found: 414.1677.

Intermediate 13

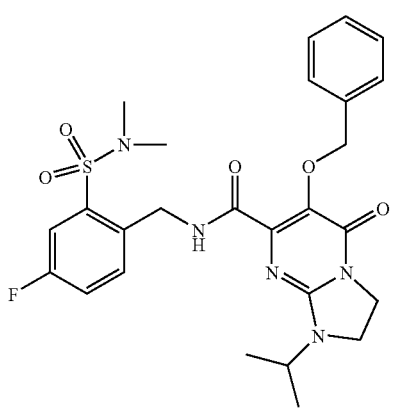

N-(4-Fluoro-2-(N,N-dimethylsulfamoyl)benzyl)-6-benzyloxy-1-isopropyl-5-oxo-1,2,3,5-tetrahydroimidazo[1,2-a]pyrimidine-7-carboxamide Coupling of 6-(benzyloxy)-1-isopropyl-5-oxo-1,2,3,5-tetrahydroimidazo[1,2-a]pyrimidine-7-carboxylic acid (0.150 g, 0.45 mmol) and 4-fluoro-2-(N,N-dimethylsulfamoyl)benzylamine hydrochloride (0.147 g, 0.55 mmol) as described for the synthesis of intermediate 3 gave 0.190 g (75% yield) of the title amide as white crystals; mp 161-163° C. (ethyl acetate-hexane). $^1$HNMR 400 MHz (CDCl$_3$) δ (ppm): 1.23 (6H, d, J=6.9 Hz, 2×CH$_3$), 2.85 (6H, s, 2×NCH$_3$), 3.65 (2H, t, J=9 Hz, CH$_2$), 4.12 (2H, t, J=9 Hz, CH$_2$), 4.40 (1H, m, CH), 4.81 (2H, d, J=6.6 Hz, NCH$_2$), 5.13 (2H, s, OCH$_2$), 7.22 (1H, m, aromatic), 7.28-7.34 (3H, m, aromatics), 7.49-7.52 (2H, m, aromatics), 7.55 (1H, dd, J=2.6 Hz and J=8.6 Hz, aromatic), 7.71 (1H, dd, J=5.6 Hz and J=8.6 Hz, aromatic), 8.26 (1H, broad t, NH). Anal. Calcd for C$_{26}$H$_{30}$FN$_5$O$_5$S: C, 57.44; H, 5.56; N, 12.88. Found: C, 57.40; H, 5.46; N, 12.85.

EXAMPLE 8

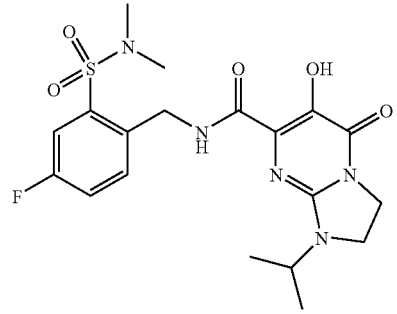

N-(4-Fluoro-2-(N,N-dimethylsulfamoyl)benzyl)-6-hydroxy-1-isopropyl-5-oxo-1,2,3,5-tetrahydroimidazo[1,2-a]pyrimidine-7-carboxamide A solution of N-(4-fluoro-2-(N,N-dimethylsulfamoyl)benzyl)-6-benzyloxy-1-isopropyl-5-oxo-1,2,3,5-tetrahydroimidazo[1,2-a]pyrimidine-7-carboxamide (0.155 g, 0.28 mmol) in trifluoroacetic acid (10 ml) was stirred at 25° C. for 72 h. The solvent was then evaporated under reduced pressure and the residue was purified by preparative HPLC (column YMC Pack C-18, 5μ, 20×250 mm, elution gradient acetonitrile-water 0.1% trifluoroacetic acid) to give 0.105 g (81% yield) of the title amide as a white solid.

$^1$HNMR 400 MHz (CDCl$_3$) δ (ppm): 1.23 (6H, d, J=6.6 Hz, 2×CH$_3$), 2.91 (6H, s, 2×NCH$_3$), 3.59 (2H, t, J=8.5 Hz, CH$_2$), 4.11 (2H, t, J=8.5 Hz, CH$_2$), 4.24 (1H, m, CH), 4.84 (2H, d, J=6.8 Hz, NCH$_2$), 7.30 (1H, m, aromatic), 7.56 (1H, dd, J=2.8 Hz and J=8.3 Hz, aromatic), 7.70 (1H, dd, J=5.3 Hz and J=8.6 Hz, aromatic), 8.52 (1H, broad t, NH), 11.4 (1H, broad, OH). MS (ESI$^+$) m/e 454 [M+H$^+$].

Intermediate 14

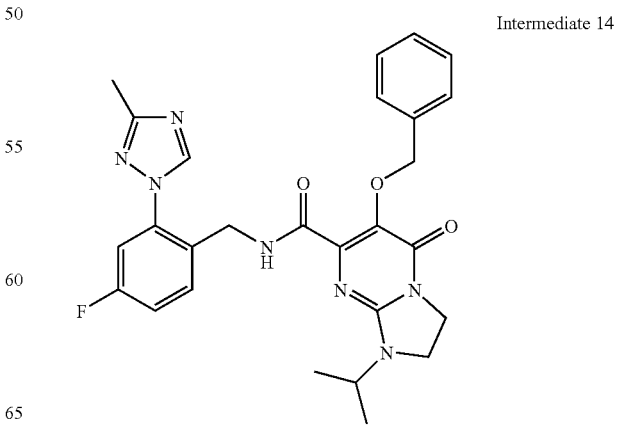

33

N-(4-Fluoro-2-(3-methyl-1H-1,2,4-triazol-1-yl)benzyl)-6-(benzyloxy)-1-isopropyl-5-oxo-1,2,3,5-tetrahydroimidazo[1,2-a]pyrimidine-7-carboxamide White crystals (ethyl acetate-hexane). (75% yield). ¹HNMR 400 MHz (CDCl₃) δ (ppm): 1.23 (6H, d, J=6.9 Hz, 2×CH₃), 2.46 (3H, s, CH₃), 3.66 (2H, t, J=8.9 Hz, CH₂), 4.13 (2H, t, J=8.9 Hz, CH₂), 4.43 (1H, m, CH), 4.44 (2H, d, J=6.3 Hz, NCH₂), 5.10 (2H, s, OCH₂), 7.05 (1H, dd, J=2.7 Hz and J=8.6 Hz, aromatic), 7.14 (1H, m, aromatic), 7.27-7.28 (3H, m, aromatics), 7.42-7.45 (2H, m, aromatics), 7.69 (1H, dd, J=6.1 Hz and J=8.6 Hz, aromatic), 8.26 (1H, broad t, NH), 8.26 (1H, s, CH). MS (ESI⁺) m/e 518 [M+H⁺].

34

N-(4-Fluoro-2-(5-methyl-1H-1,2,4-triazol-1-yl)benzyl)-6-(benzyloxy)-1-isopropyl-5-oxo-1,2,3,5-tetrahydroimidazo[1,2-a]pyrimidine-7-carboxamide White crystals; mp 158-159° C. (ethyl acetate). (71% yield). ¹HNMR 400 MHz (CDCl₃) δ (ppm): 1.24 (6H, d, J=6.5 Hz, 2×CH₃), 2.44 (3H, s, CH₃), 3.66 (2H, t, J=8.8 Hz, CH₂), 4.13 (2H, t, J=8.8 Hz, CH₂), 4.23 (2H, d, J=6.3 Hz, NCH₂), 4.44 (1H, m, CH), 5.11 (2H, s, OCH₂), 6.99 (1H, dd, J=2.5 Hz and J=8.3 Hz, aromatic), 7.18 (1H, m, aromatic), 7.29-7.34 (3H, m, aromatics), 7.48-7.50 (2H, m, aromatics), 7.66 (1H, dd, J=6.0 Hz and J=8.7 Hz, aromatic), 7.89 (1H, s, CH), 8.10 (1H, broad t, NH). MS (ESI⁺) m/e 518 [M+H⁺].

EXAMPLE 9

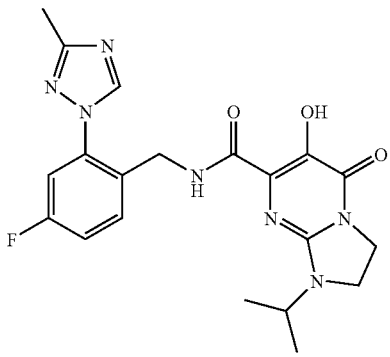

N-(4-Fluoro-2-(3-methyl-1H-1,2,4-triazol-1-yl)benzyl)-6-hydroxy-1-isopropyl-5-oxo-1,2,3,5-tetrahydroimidazo[1,2-a]pyrimidine-7-carboxamide White solid (100% yield). ¹HNMR 400 MHz (CDCl₃) δ (ppm): 1.24 (6H, d, J=6.6 Hz, 2×CH₃), 2.55 (3H, s, CH₃), 3.60 (2H, t, J=8.5 Hz, CH₂), 4.12 (2H, t, J=8.5 Hz, CH₂), 4.31 (1H, m, CH), 4.49 (2H, d, J=6.6 Hz, NCH₂), 7.10 (1H, dd, J=2.5 Hz and J=8.3 Hz, aromatic), 7.20 (1H, m, aromatic), 7.70 (1H, dd, J=6.0 Hz and J=8.7 Hz, aromatic), 8.35 (1H, s, CH), 8.61 (1H, broad t, NH), 11.56 (1H, s, OH). MS (ESI⁺) m/e 428 [M+H⁺].

EXAMPLE 10

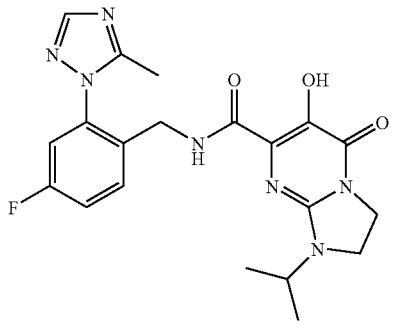

N-(4-Fluoro-2-(5-methyl-1H-1,2,4-triazol-1-yl)benzyl)-6-hydroxy-1-isopropyl-5-oxo-1,2,3,5-tetrahydroimidazo[1,2-a]pyrimidine-7-carboxamide White crystals; mp 212° C. (ethyl acetate). (61% yield). ¹HNMR 400 MHz (CDCl₃) δ (ppm): 1.27 (6H, d, J=6.8 Hz, 2×CH₃), 2.47 (3H, s, CH₃), 3.60 (2H, t, J=8.6 Hz, CH₂), 4.11 (2H, t, J=8.6 Hz, CH₂), 4.28 (1H, m, CH), 4.31 (2H, d, J=6.5 Hz, NCH₂), 7.03 (1H, dd, J=2.8 Hz and J=8.3 Hz, aromatic), 7.26 (1H, m, aromatic), 7.67 (1H, dd, J=6.0 Hz and J=8.6 Hz, aromatic), 8.00 (1H, s, CH), 8.35 (1H, broad t, NH), 11.35 (1H, s, OH). MS (ESI⁺) m/e 428 [M+H⁺].

Intermediate 15

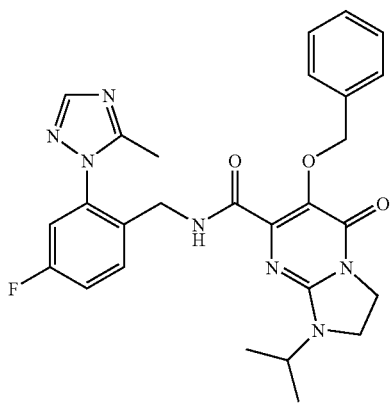

Intermediate 16

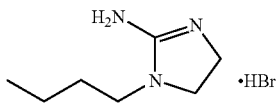

1-Butyl-4,5-dihydro-1H-imidazol-2-amine hydrobromide

Reaction of N-butylethylenediamine (10.7 g, 0.092 mol) with cyanogen bromide (9.76 g, 0.092 mol) as described in the preparation of intermediate 6 gave 11.77 g (57% yield) of the title compound as white crystals (ether-hexane). ¹HNMR 400 MHz (CDCl₃) δ (ppm): 0.96 (3H, t, J=7.2 Hz, CH₃), 1.41 (2H, m, CH₂), 1.60 (2H, m, CH₂), 3.52 (2H, t, J=7.3 Hz, CH₂), 3.64-3.74 (4H, m, 2×CH₂), 7.58 and 7.7 (broad s, NH). MS (ESI⁺) m/e 142 [M+H⁺].

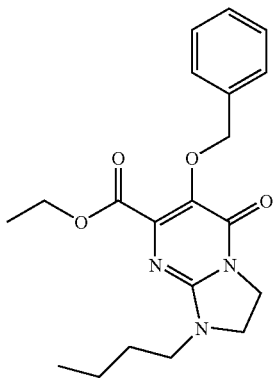

Intermediate 17

Ethyl 6-(benzyloxy)-1-butyl-5-oxo-1,2,3,5-tetrahydroimidazo[1,2-a]pyrimidine-7-carboxylate Reaction of the adduct of diethyl oxalate (5.71 g, 39.1 mmol), ethyl benzyloxyacetate (7.59 g, 39.1 mmol) and sodium hydride (1.71 g of a 60% dispersion in mineral oil, 42.7 mmol) with 1-butyl-4,5-dihydro-1H-imidazol-2-amine hydrobromide (8.68 g, 39.1 mmol) as described for intermediate 1 gave 5.55 g (38% yield) of the title ester as a clear oil. $^1$HNMR 400 MHz (CDCl$_3$) δ (ppm): 0.98 (3H, t, J=7.5 Hz, CH$_3$), 1.31 (3H, t, J=7.1 Hz, CH$_3$), 1.39 (2H, m, CH$_2$), 1.56-1.63 (2H, m, CH$_2$), 3.41 (2H, t, J=7.4 Hz, CH$_2$), 3.69 (2H, t, J=8.9 Hz, CH$_2$), 4.12 (2H, t, J=8.9 Hz, CH$_2$), 4.32 (2H, q, J=7.1 Hz, OCH$_2$), 5.09 (2H, s, OCH$_2$), 7.3-7.4 (3H, m, aromatics), 7.49 (2H, m, aromatics). MS (ESI$^+$) m/e 372 [M+H$^+$].

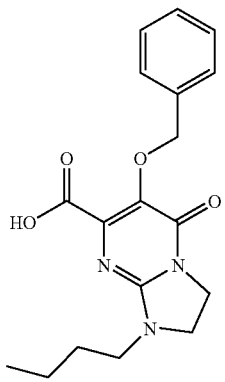

Intermediate 18

6-(Benzyloxy)-1-butyl-5-oxo-1,2,3,5-tetrahydroimidazo[1,2-a]pyrimidine-7-carboxylic Acid Saponification of ethyl 6-(benzyloxy)-1-butyl-5-oxo-1,2,3,5-tetrahydroimidazo[1,2-a]pyrimidine-7-carboxylate (5.50 g, 14.8 mmol) as described for intermediate 2 gave 5.08 g (100% yield) of the title acid as a white solid; mp 132-135° C. (ethyl acetate). $^1$HNMR 400 MHz (CDCl$_3$) δ (ppm): 0.98 (3H, t, J=7.3 Hz, CH$_3$), 1.34-1.44 (2H, m, CH$_2$), 1.56-1.63 (2H, m, CH$_2$), 3.39 (2H, t, J=7.4 Hz, CH$_2$), 3.71 (2H, t, J=8.9 Hz, CH$_2$), 4.15 (2H, t, J=8.9 Hz, CH$_2$), 5.23 (2H, s, OCH$_2$), 7.3-7.4 (3H, m, aromatics), 7.58 (2H, m, aromatics). MS (ESI$^+$) m/e 344 [M+H$^+$].

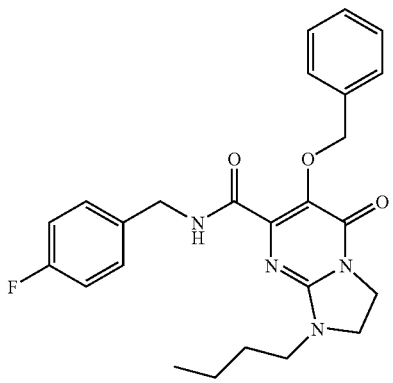

Intermediate 19

N-(4-Fluorobenzyl)-6-(benzyloxy)-1-butyl-5-oxo-1,2,3,5-tetrahydroimidazo[1,2-a]pyrimidine-7-carboxamide Coupling of 6-(benzyloxy)-1-butyl-5-oxo-1,2,3,5-tetrahydroimidazo[1,2-a]pyrimidine-7-carboxylic acid (0.300 g, 0.87 mmol) and 4-fluorobenzylamine (0.120 g, 0.96 mmol) as described for the synthesis of intermediate 3 gave 0.349 g (88% yield) of the title amide as white crystals; mp 107-109° C. (ethyl acetate-hexane). $^1$HNMR 400 MHz (CDCl$_3$) δ (ppm): 0.96 (3H, t, J=7.3 Hz, CH$_3$), 1.33-1.43 (2H, m, CH$_2$), 1.56-1.63 (2H, m, CH$_2$), 3.41 (2H, t, J=7.4 Hz, CH$_2$), 3.70 (2H, t, J=8.9 Hz, CH$_2$), 4.13 (2H, t, J=8.9 Hz, CH$_2$), 4.50 (2H, d, J=5.8 Hz, NCH$_2$), 5.10 (2H, s, OCH$_2$), 7.0 (2H, m, aromatics), 7.25 (2H, m, aromatics), 7.33-7.37 (3H, m, aromatics), 7.46-7.48 (2H, m, aromatics), 7.68 (1H, broad t, NH). MS (ESI$^+$) m/e 451 [M+H$^+$].

EXAMPLE 11

N-(4-Fluorobenzyl)-1-butyl-6-hydroxy-5-oxo-1,2,3,5-tetrahydroimidazo[1,2-a]pyrimidine-7-carboxamide Hydrogenolysis of N-(4-fluorobenzyl)-6-(benzyloxy)-1-butyl-5-oxo-1,2,3,5-tetrahydroimidazo[1,2-a]pyrimidine-7-carboxamide (0.350 g, 0.77 mmol) as described for example 1 gave 0.278 g (99% yield) of the title compound as a white solid. $^1$HNMR 400 MHz (CDCl$_3$) δ (ppm): 0.95 (3H, t, J=7.3 Hz, CH$_3$), 1.33-1.42 (2H, m, CH$_2$), 1.54-1.67 (2H, m, CH$_2$), 3.31 (2H, t, J=7.2 Hz, CH$_2$), 3.63 (2H, t, J=8.9 Hz, CH$_2$), 4.14 (2H, t, J=8.9 Hz, CH$_2$), 4.59 (2H, d, J=6.3 Hz, NCH$_2$), 7.07 (2H, m, aromatics), 7.33 (2H, m, aromatics), 7.86 (1H, broad t, NH), 11.52 (1H, s, OH). MS (ESI$^+$) m/e 361 [M+H$^+$].

Intermediate 20

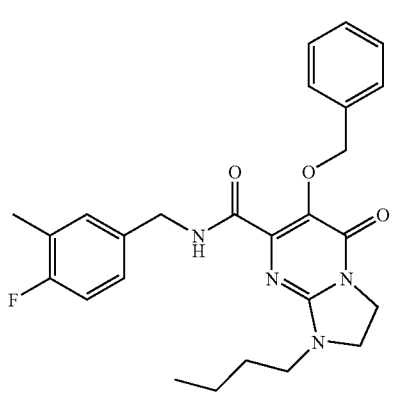

N-(4-Fluoro-3-methylbenzyl)-6-(benzyloxy)-1-butyl-5-oxo-1,2,3,5-tetrahydroimidazo[1,2-a]pyrimidine-7-carboxamide White solid, (90% yield).

$^1$HNMR 400 MHz (CDCl$_3$) δ (ppm): 0.96 (3H, t, J=7.3 Hz, CH$_3$), 1.35-1.43 (2H, m, CH$_2$), 1.56-1.63 (2H, m, CH$_2$), 2.25 (3H, d, J=1.8 Hz, CH$_3$), 3.41 (2H, t, J=7.5 Hz, CH$_2$), 3.70 (2H, t, J=8.9 Hz, CH$_2$), 4.15 (2H, t, J=8.9 Hz, CH$_2$), 4.46 (2H, d, J=5.8 Hz, NCH$_2$), 5.09 (2H, s, OCH$_2$), 6.94 (1H, m, aromatic), 7.04-7.07 (1H, m, aromatic), 7.10 (1H, d, J=7.2 Hz, aromatic), 7.30-7.36 (3H, m, aromatics), 7.44-7.47 (2H, m, aromatics), 7.67 (1H, broad t, NH). MS (ESI$^+$) m/e 465 [M+H$^+$].

EXAMPLE 12

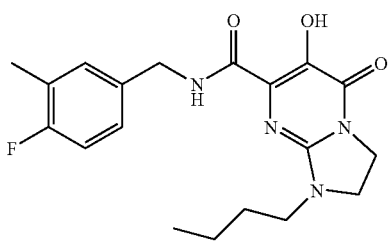

N-(4-Fluoro-3-methylbenzyl)-1-butyl-6-hydroxy-5-oxo-1,2,3,5-tetrahydroimidazo[1,2-a]pyrimidine-7-carboxamide White solid (94% yield). $^1$HNMR 400 MHz (CDCl$_3$) δ (ppm): 0.95 (3H, t, J=7.3 Hz, CH$_3$), 1.28-1.42 (2H, m, CH$_2$), 1.54-1.63 (2H, m, CH$_2$), 2.29 (3H, d, J=1.8 Hz, CH$_3$), 3.31 (2H, t, J=7.3 Hz, CH$_2$), 3.63 (2H, t, J=8.9 Hz, CH$_2$), 4.14 (2H, t, J=8.9 Hz, CH$_2$), 4.54 (2H, d, J=6.4 Hz, NCH$_2$), 7.0 (1H, m, aromatic), 7.11-7.17 (2H, m, aromatics), 7.84 (1H, broad t, NH), 11.55 (1H, s, OH). MS (ESI$^+$) m/e 375 [M+H$^+$].

Intermediate 21

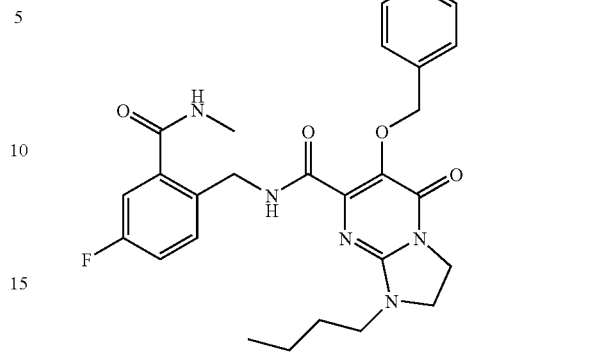

N-(4-Fluoro-2-(methylcarbamoyl)benzyl)-6-(benzyloxy)-1-butyl-5-oxo-1,2,3,5-tetrahydroimidazo[1,2-a]pyrimidine-7-carboxamide White solid, (87% yield). $^1$HNMR 400 MHz (CDCl$_3$) δ (ppm): 0.97 (3H, t, J=7.3 Hz, CH$_3$), 1.37-1.44 (2H, m, CH$_2$), 1.56-1.63 (2H, m, CH$_2$), 2.98 (3H, d, J=4.8 Hz, CH$_3$), 3.42 (2H, t, J=7.4 Hz, CH$_2$), 3.68 (2H, t, J=8.7 Hz, CH$_2$), 4.12 (2H, t, J=8.7 Hz, CH$_2$), 4.48 (2H, d, J=6.3 Hz, NCH$_2$), 5.10 (2H, s, OCH$_2$), 7.02-7.09 (2H, m, aromatic and NH), 7.14 (1H, dd, J=2.8 Hz and J=8.9 Hz, aromatic), 7.30-7.37 (4H, m, aromatics), 7.44-7.49 (2H, m, aromatics), 8.42 (1H, broad t, NH). MS (ESI$^+$) m/e 508 [M+H$^+$].

EXAMPLE 13

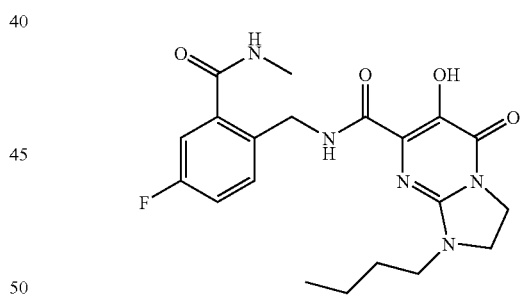

N-(4-Fluoro-2-(methylcarbamoyl)benzyl)-1-butyl-6-hydroxy-5-oxo-1,2,3,5-tetrahydroimidazo[1,2-a]pyrimidine-7-carboxamide White crystals; mp 175-177° C. (ethyl acetate). (92% yield). $^1$HNMR 400 MHz (CDCl$_3$) δ (ppm): 0.99 (3H, t, J=7.3 Hz, CH$_3$), 1.40-1.45 (2H, m, CH$_2$), 1.58-1.64 (2H, m, CH$_2$), 3.03 (3H, d, J=5.0 Hz, CH$_3$), 3.38 (2H, t, J=7.4 Hz, CH$_2$), 3.61 (2H, t, J=8.5 Hz, CH$_2$), 4.10 (2H, t, J=8.5 Hz, CH$_2$), 4.59 (2H, d, J=6.5 Hz, NCH$_2$), 6.40 (1H, broad q, NH), 7.11-7.15 (1H, m, aromatic), 7.18 (1H, dd, J=2.7 Hz and J=8.8 Hz, aromatic), 7.48 (1H, dd, J=5.4 Hz and J=8.5 Hz, aromatic), 8.81 (1H, broad t, NH), 11.48 (1H, s, OH). MS (ESI$^+$) m/e 418 [M+H$^+$].

Intermediate 22

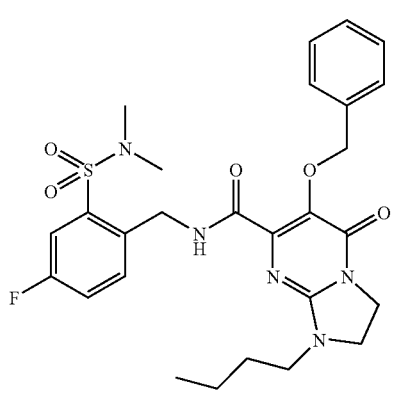

N-(4-Fluoro-2-(N,N-dimethylsulfamoyl)benzyl)-6-(benzyloxy)-1-butyl-5-oxo-1,2,3,5-tetrahydroimidazo[1,2-a]pyrimidine-7-carboxamide White solid, (95% yield). $^1$HNMR 400 MHz (CDCl$_3$) δ (ppm): 0.96 (3H, t, J=7.3 Hz, CH$_3$), 1.34-1.44 (2H, m, CH$_2$), 1.55-1.66 (2H, m, CH$_2$), 2.85 (6H, s, 2×NCH$_3$), 3.41 (2H, t, J=7.4 Hz, CH$_2$), 3.68 (2H, t, J=8.7 Hz, CH$_2$), 4.12 (2H, t, J=8.7 Hz, CH$_2$), 4.80 (2H, d, J=6.6 Hz, NCH$_2$), 5.12 (2H, s, OCH$_2$), 7.2-7.25 (1H, m, aromatic), 7.27-7.34 (3H, m, aromatics), 7.50-7.52 (2H, m, aromatics), 7.55 (1H, dd, J=2.7 Hz and J=8.5 Hz, aromatic), 7.71 (1H, dd, J=5.3 Hz and J=8.6 Hz, aromatic), 8.30 (1H, broad t, NH). MS (ESI$^+$) m/e 558 [M+H$^+$].

Intermediate 23

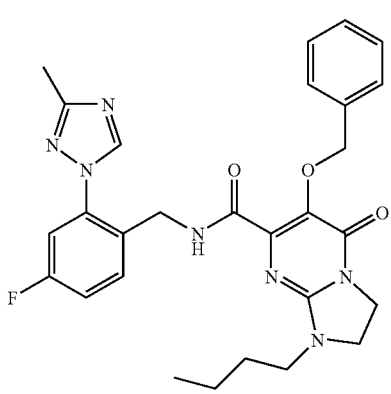

N-(4-Fluoro-2-(3-methyl-1H-1,2,4-triazol-1-yl)benzyl)-6-(benzyloxy)-1-butyl-5-oxo-1,2,3,5-tetrahydroimidazo[1,2-a]pyrimidine-7-carboxamide White crystals; mp 172-173° C. (ethyl acetate-hexane). (64% yield). $^1$HNMR 400 MHz (CDCl$_3$) δ (ppm): 0.94 (3H, t, J=7.3 Hz, CH$_3$), 1.33-1.42 (2H, m, CH$_2$), 1.55-1.63 (2H, m, CH$_2$), 2.47 (3H, s, CH$_3$), 3.42 (2H, t, J=7.4 Hz, CH$_2$), 3.69 (2H, t, J=8.8 Hz, CH$_2$), 4.14 (2H, t, J=8.8 Hz, CH$_2$), 4.42 (2H, d, J=6.3 Hz, NCH$_2$), 5.11 (2H, s, OCH$_2$), 7.05 (1H, dd, J=2.7 Hz and J=8.5 Hz, aromatic), 7.11-7.16 (1H, m, aromatic), 7.24-7.28 (3H, m, aromatics), 7.41-7.44 (2H, m, aromatics), 7.68 (1H, dd, J=6.0 Hz and J=8.6 Hz, aromatic), 8.24 (1H, broad t, NH), 8.29 (1H, s, CH). MS (ESI$^+$) m/e 532 [M+H$^+$]. Anal. Calcd for C$_{28}$H$_{30}$FN$_7$O$_3$: C, 63.26; H, 5.68; N, 18.44. Found: C, 63.18; H, 5.79; N, 18.32.

EXAMPLE 14

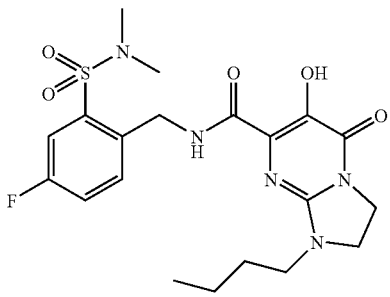

N-(4-Fluoro-2-(N,N-dimethylsulfamoyl)benzyl)-1-butyl-6-hydroxy-5-oxo-1,2,3,5-tetrahydroimidazo[1,2-a]pyrimidine-7-carboxamide White solid (91% yield). $^1$HNMR 400 MHz (CDCl$_3$) δ (ppm): 0.98 (3H, t, J=7.3 Hz, CH$_3$), 1.30-1.44 (2H, m, CH$_2$), 1.56-1.63 (2H, m, CH$_2$), 2.91 (6H, s, 2×NCH$_3$), 3.34 (2H, t, J=7.2 Hz, CH$_2$), 3.62 (2H, t, J=8.4 Hz, CH$_2$), 4.12 (2H, t, J=8.4 Hz, CH$_2$), 4.83 (2H, d, J=6.8 Hz, NCH$_2$), 7.26-7.31 (1H, m, aromatic), 7.55 (1H, dd, J=2.6 Hz and J=8.4 Hz, aromatic), 7.69 (1H, dd, J=5.3 Hz and J=8.6 Hz, aromatic), 8.55 (1H, broad t, NH), 11.40 (1H, s, OH). MS (ESI$^+$) m/e 468 [M+H$^+$].

EXAMPLE 15

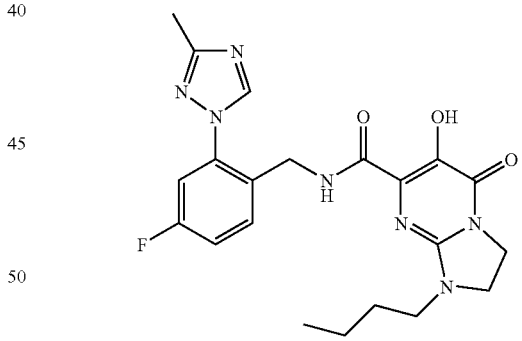

N-(4-Fluoro-2-(3-methyl-1H-1,2,4-triazol-1-yl)benzyl)-1-butyl-6-hydroxy-5-oxo-1,2,3,5-tetrahydroimidazo[1,2-a]pyrimidine-7-carboxamide White crystals; mp 214° C. (ethyl acetate). (93% yield). $^1$HNMR 400 MHz (CDCl$_3$) δ (ppm): 0.95 (3H, t, J=7.4 Hz, CH$_3$), 1.33-1.43 (2H, m, CH$_2$), 1.56-1.64 (2H, m, CH$_2$), 2.55 (3H, s, CH$_3$), 3.38 (2H, t, J=7.2 Hz, CH$_2$), 3.62 (2H, t, J=8.5 Hz, CH$_2$), 4.13 (2H, t, J=8.5 Hz, CH$_2$), 4.49 (2H, d, J=6.5 Hz, NCH$_2$), 7.09 (1H, dd, J=2.6 Hz and J=8.4 Hz, aromatic), 7.17-7.22 (1H, m, aromatic), 7.69 (1H, dd, J=6.1 Hz and J=8.6 Hz, aromatic), 8.32 (1H, s, CH), 8.57 (1H, broad t, NH), 11.60 (1H, s, OH). MS (ESI$^+$) m/e 442 [M+H$^+$].

Intermediate 24

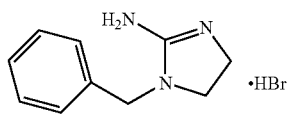

1-Benzyl-4,5-dihydro-1H-imidazol-2-amine hydrobromide

Reaction of N-benzylethylenediamine (15.02 g, 0.10 mol) with cyanogen bromide (10.6 g, 0.10 mol) as described in the preparation of intermediate 6 gave 23.82 g (93% yield) of the title product as white crystals; mp 202-204° C. (ethanol). $^1$HNMR 400 MHz (DMSO-$d_6$) δ (ppm): 3.48-3.56 (4H, m, 2×$CH_2$), 4.57 (2H, m, $NCH_2$), 7.30-7.44 (5H, m, aromatics), 7.92 and 8.18 (broad s, NH). Anal. Calcd for $C_{10}H_{13}N_3$·HBr: C, 46.89, H 5.50; N, 16.40. Found: C, 47.03; H, 5.49; N, 16.24.

Intermediate 25

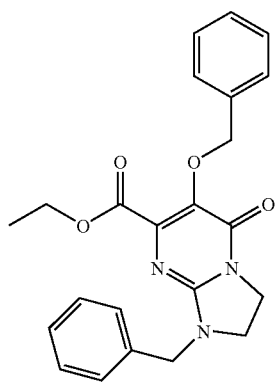

Ethyl 1-benzyl-6-(benzyloxy)-5-oxo-1,2,3,5-tetrahydroimidazo[1,2-a]pyrimidine-7-carboxylate Reaction of the adduct of diethyl oxalate (7.66 g, 52.4 mmol), ethyl benzyloxyacetate (10.2 g, 52.5 mmol) and sodium hydride (2.31 g of a 60% dispersion in mineral oil, 57.9 mmol) with 1-benzyl-4,5-dihydro-1H-imidazol-2-amine hydrobromide (13.39 g, 52.5 mmol) as described for intermediate 1 gave 3.98 g (18% yield) of the title ester as white crystals; mp 93° C. (ethyl acetate-hexane).

$^1$HNMR 400 MHz ($CDCl_3$) δ (ppm): 1.33 (3H, t, J=7.1 Hz, $CH_3$), 3.56 (2H, t, J=9.1 Hz, $CH_2$), 4.12 (2H, t, J=9.1 Hz, $CH_2$), 4.35 (2H, q, J=7.1 Hz, $OCH_2$), 4.60 (2H, s, $NCH_2$), 5.12 (2H, s, $OCH_2$), 7.3-7.52 (10H, m, aromatics). Anal. Calcd for $C_{23}H_{23}N_3O_4$: C, 68.13; H, 5.71; N, 10.36. Found: C, 67.98; H, 5.70; N, 10.40.

Intermediate 26

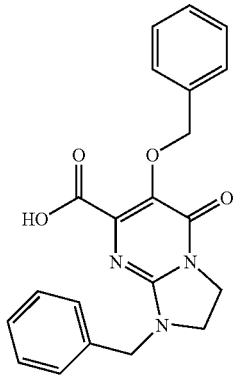

1-Benzyl-6-(benzyloxy)-5-oxo-1,2,3,5-tetrahydroimidazo[1,2-a]pyrimidine-7-carboxylic acid Saponification of ethyl 1-benzyl-6-(benzyloxy)-5-oxo-1,2,3,5-tetrahydroimidazo[1,2-a]pyrimidine-7-carboxylate (2.04 g, 5.04 mmol) as described for intermediate 2 gave 1.90 g (100% yield) of the title acid as white crystals; mp 191° C. (dec), (ethyl acetate). $^1$HNMR 400 MHz (DMSO-$d_6$,) δ (ppm): 3.58 (2H, t, J=8.8 Hz, $CH_2$), 4.05 (2H, t, J=8.8 Hz, $CH_2$), 4.53 (2H, s, $NCH_2$), 4.93 (2H, s, $OCH_2$), 7.32-7.45 (10H, m, aromatics), 13.41 (1H, s, OH). Anal. Calcd for $C_{21}H_{19}N_3O_4$: C 66.83; H, 5.07; N, 11.13. Found: C, 66.73; H, 5.16; N, 10.97.

Intermediate 27

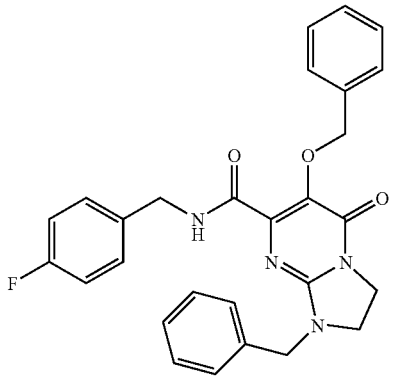

N-(4-Fluorobenzyl)-1-benzyl-6-(benzyloxy)-5-oxo-1,2,3,5-tetrahydroimidazo[1,2-a]pyrimidine-7-carboxamide White crystals; mp 125° C. (ethyl acetate-hexane). (88% yield). $^1$HNMR 400 MHz ($CDCl_3$) δ (ppm): 3.58 (2H, t, J=8.7 Hz, $CH_2$), 4.13 (2H, t, J=8.7 Hz, $CH_2$), 4.51 (2H, d, J=6.1 Hz, $NCH_2$), 4.60 (2H, s, $NCH_2$), 5.13 (2H, s, $OCH_2$), 7.0 (2H, m, aromatics), 7.24-7.38 (10H, m, aromatics), 7.47-7.49 (2H, m, aromatics), 7.71 (1H, broad t, NH). HRMS (ESI⁺) calculated for $C_{28}H_{26}FN_4O_3$ [M+H⁺]: 485.1989. found: 485.1993.

EXAMPLE 16

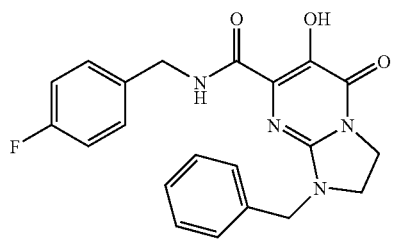

N-(4-Fluorobenzyl)-1-benzyl-6-hydroxy-5-oxo-1,2,3,5-tetrahydroimidazo[1,2-a]pyrimidine-7-carboxamide White crystals; mp 225° C. (ethyl acetate-hexane). (97% yield). ¹HNMR 400 MHz (CDCl₃) δ (ppm): 3.53 (2H, t, J=8.6 Hz, CH₂), 4.13 (2H, t, J=8.6 Hz, CH₂), 4.50 (2H, s, NCH₂), 4.59 (2H, d, J=6.1 Hz, NCH₂), 7.06 (2H, m, aromatics), 7.25-7.4 (7H, m, aromatics), 7.87 (1H, broad t, NH), 11.60 (1H, s, OH). HRMS (ESI⁺) calculated for $C_{21}H_{20}FN_4O_3$ [M+H⁺]: 395.1519. found: 395.1508.

7.47-7.49 (2H, m, aromatics), 7.69 (1H, broad t, NH). HRMS (ESI⁺) calculated for $C_{29}H_{28}FN_4O_3$ [M+H⁺]: 499.2145. found: 499.2132.

EXAMPLE 17

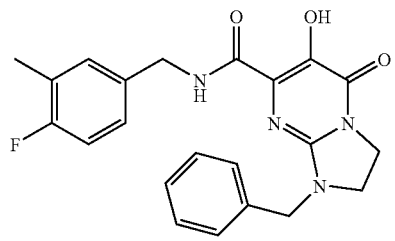

N-(4-Fluoro-3-methylbenzyl)-1-benzyl-6-hydroxy-5-oxo-1,2,3,5-tetrahydroimidazo[1,2-a]pyrimidine-7-carboxamide White crystals; mp 204° C. (dec) (ethyl acetate). (78% yield). ¹HNMR 400 MHz (CDCl₃) δ (ppm): 2.29 (3H, s, CH₃), 3.53 (2H, t, J=8.5 Hz, CH₂), 4.13 (2H, t, J=8.5 Hz, CH₂), 4.50 (2H, s, NCH₂), 4.54 (2H, d, J=6.0 Hz, NCH₂), 7.02 (1H, m, aromatics), 7.1-7.4 (7H, m, aromatics), 7.84 (1H, broad t, NH), 11.63 (1H, s, OH). Anal. Calcd for $C_{22}H_{22}FN_4O_3$: C, 64.69; H, 5.18; N, 13.71. Found: C, 64.42; H, 5.26; N, 13.55.

Intermediate 28

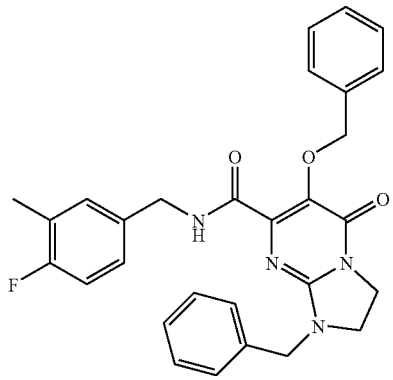

N-(4-Fluoro-3-methylbenzyl)-1-benzyl-6-(benzyloxy)-5-oxo-1,2,3,5-tetrahydroimidazo[1,2-a]pyrimidine-7-carboxamide White crystals. (81% yield). ¹HNMR 400 MHz (CDCl₃) δ (ppm): 2.24 (3H, s, CH₃), 3.57 (2H, t, J=8.7 Hz, CH₂), 4.12 (2H, t, J=8.7 Hz, CH₂), 4.47 (2H, d, J=5.6 Hz, NCH₂), 4.58 (2H, s, NCH₂), 5.12 (2H, s, OCH₂), 6.93 (1H, m, aromatic), 7.05-7.12 (2H, m, aromatics), 7.28-7.40 (8H, m, aromatics), Intermediate 29

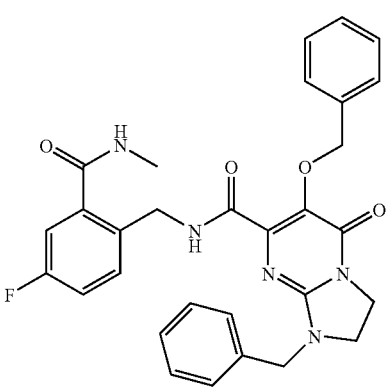

N-(4-Fluoro-2-(methylcarbamoyl)benzyl)-1-benzyl-6-(benzyloxy)-5-oxo-1,2,3,5-tetrahydroimidazo[1,2-a]pyrimidine-7-carboxamide White solid (95% yield). ¹HNMR 400 MHz (CDCl₃) δ (ppm): 2.97 (3H, d, J=5.14 Hz, CH₃), 3.55 (2H, t, J=8.8 Hz, CH₂), 4.09 (2H, t, J=8.8 Hz, CH₂), 4.50 (2H, d, J=6.28 Hz, NCH₂), 4.60 (2H, s, NCH₂), 5.12 (2H, s, OCH₂), 7.03-7.08 (2H, m, aromatics), 7.14 (1H, dd, J=2.5 Hz and J=8.6 Hz, aromatic), 7.28-7.48 (9H, m, NH and aromatics), 7.54-7.57

(2H, m, aromatics), 8.46 (1H, broad t, NH). HRMS (ESI⁺) calculated for $C_{30}H_{29}FN_5O_4$ [M+H⁺]: 542.2204. found: 542.2214.

EXAMPLE 18

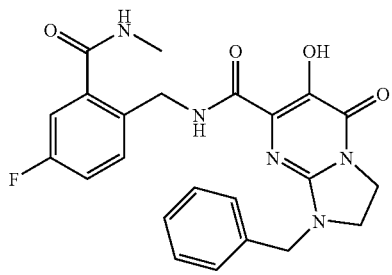

N-(4-Fluoro-2-(methylcarbamoyl)benzyl)-1-benzyl-6-hydroxy-5-oxo-1,2,3,5-tetrahydroimidazo[1,2-a]pyrimidine-7-carboxamide White crystals; mp 206° C. (dec) (ethyl acetate). (72% yield). ¹HNMR 400 MHz (DMSO-d₆) δ (ppm): 2.75 (3H, d, J=4.4 Hz, NCH₃), 3.49 (2H, t, J=8.3 Hz, CH₂), 3.99 (2H, t, J=8.3 Hz, CH₂), 4.54 (2H, d, J=6.0 Hz, NCH₂), 4.57 (2H, s, NCH₂), 7.25-7.4 (8H, m, aromatics), 8.53 (1H, broad, NH), 9.31 (1H, broad, NH), 11.64 (1H, s, OH). HRMS (ESI⁺) calculated for $C_{23}H_{23}FN_5O_4$ [M+H⁺]: 452.1734. found: 452.1720.

Intermediate 30

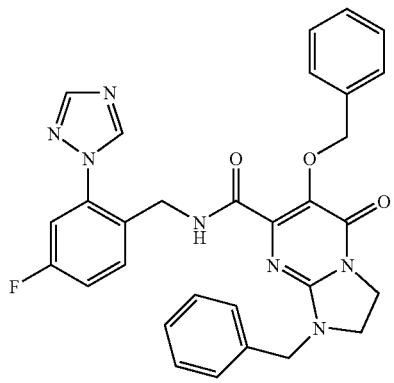

N-(4-Fluoro-2-(1H-1,2,4-triazol-1-yl)benzyl)-1-benzyl-6-(benzyloxy)-5-oxo-1,2,3,5-tetrahydroimidazo[1,2-a]pyrimidine-7-carboxamide White solid (91% yield). ¹HNMR 400 MHz (DMSO-d₆) δ (ppm): 3.57 (2H, t, J=8.7 Hz, CH₂), 4.04 (2H, t, J=8.7 Hz, CH₂), 4.30 (2H, d, J=6.05 Hz, NCH₂), 4.57 (2H, s, NCH₂), 4.91 (2H, s, OCH₂), 7.16 (1H, m, aromatic), 7.29-7.53 (12H, m, aromatics), 8.23 (1H, s, CH), 8.88 (1H, broad t, NH), 8.99 (1H, s, CH). HRMS (ESI⁺) calculated for $C_{30}H_{27}FN_7O_3$ [M+H⁺]: 552.2159. found: 552.2173.

EXAMPLE 19

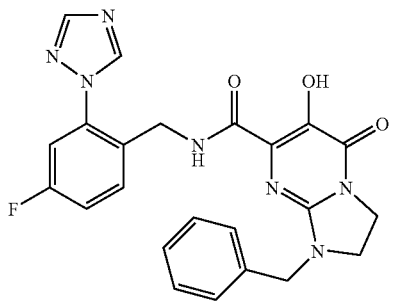

N-(4-Fluoro-2-(1H-1,2,4-triazol-1-yl)benzyl)-1-benzyl-6-hydroxy-5-oxo-1,2,3,5-tetrahydroimidazo[1,2-a]pyrimidine-7-carboxamide White crystals; mp 242° C. (dec) (ethyl acetate). (74% yield). ¹HNMR 400 MHz (DMSO-d₆) δ (ppm): 3.49 (2H, t, J=8.4 Hz, CH₂), 4.00 (2H, t, J=8.4 Hz, CH₂), 4.41 (2H, d, J=6.2 Hz, NCH₂), 4.61 (2H, s, NCH₂), 7.3-7.56 (8H, m, aromatics), 8.24 (1H, s, CH), 9.03 (1H, s, CH), 9.28 (1H, broad t, NH), 11.49 (1H, s, OH). HRMS (ESI⁺) calculated for $C_{23}H_{21}FN_7O_3$ [M+H⁺]: 462.1690. found: 462.1682.

Intermediate 31

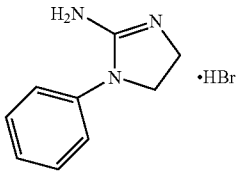

1-Phenyl-4,5-dihydro-1H-imidazol-2-amine hydrobromide

Reaction of N-phenylethylenediamine (9.80 g, 0.072 mol) with cyanogen bromide (7.62 g, 0.072 mol) as described in the preparation of intermediate 6 gave 11.76 g (67% yield) of the title product as white crystals from ethanol. ¹HNMR 400 MHz (DMSO-d,) δ (ppm): 3.68 (2H, t, J=8.7 Hz, CH₂), 4.08 (2H, t, J=8.7 Hz, CH₂), 7.40-7.54 (5H, m, aromatics), 8.08 (broad s, NH). MS (ESI⁺) m/e 162 [M+H⁺].

Intermediate 32

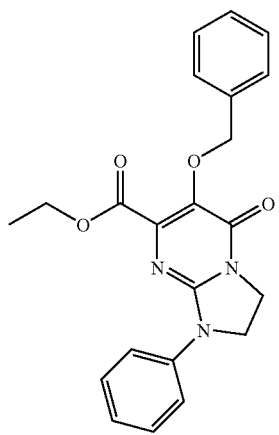

Ethyl 6-(benzyloxy)-5-oxo-1-phenyl-1,2,3,5-tetrahydroimidazo[1,2-a]pyrimidine-7-carboxylate Reaction of the adduct of diethyl oxalate (7.06 g, 48.3 mmol), ethyl benzyloxyacetate (9.38 g, 48.3 mmol) and sodium hydride (2.12 g of a 60% dispersion in mineral oil, 53.1 mmol) with 1-phenyl-4,5-dihydro-1H-imidazol-2-amine hydrobromide (11.70 g, 48.3 mmol) as described for intermediate 1 gave 1.99 g (11% yield) of the title ester as white crystals; mp 132-134° C. (ethyl acetate-hexane). $^1$HNMR 400 MHz (CDCl$_3$) δ (ppm): 1.33 (3H, t, J=7.1 Hz, CH$_3$), 4.23-4.29 (4H, m, 2×CH$_2$), 4.35 (2H, q, J=7.1 Hz, OCH$_2$), 5.18 (2H, s, OCH$_2$), 7.16 (1H, m, aromatic), 7.3-7.53 (7H, m, aromatics), 7.73 (2H, m, aromatics). Anal. Calcd for C$_{22}$H$_{21}$N$_3$O$_4$: C, 67.50; H, 5.40; N, 10.73. Found: C, 67.44; H, 5.68; N, 10.73.

Intermediate 33

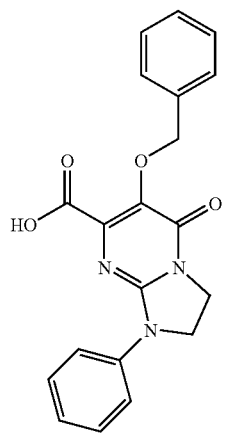

6-(Benzyloxy)-5-oxo-1-phenyl-1,2,3,5-tetrahydroimidazo[1,2-a]pyrimidine-7-carboxylic Acid Saponification of ethyl 6-(benzyloxy)-5-oxo-1-phenyl-1,2,3,5-tetrahydroimidazo[1,2-a]pyrimidine-7-carboxylate (1.94 g, 4.95 mmol) as described for intermediate 2 gave 1.78 g (98% yield) of the title acid as white crystals. $^1$HNMR 400 MHz (DMSO-d$_6$) δ (ppm): 4.17-4.20 (4H, m, 2×CH$_2$), 5.00 (2H, s, OCH$_2$), 7.13 (1H, m, aromatic), 7.35-7.46 (7H, m, aromatics), 7.78 (2H, m, aromatics), 13.52 (1H, s, OH). HRMS (ESI$^+$) calculated for C$_{20}$H$_{18}$N$_3$O$_4$ [M+H$^+$]: 364.1297. found: 364.1292.

Intermediate 34

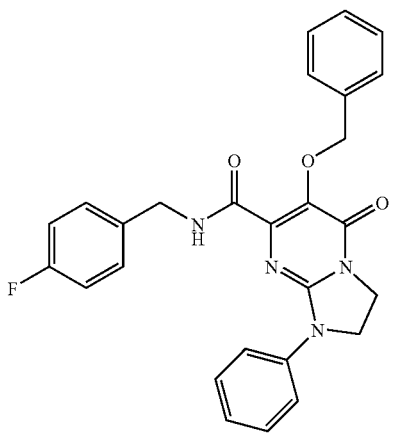

N-(4-Fluorobenzyl)-6-(benzyloxy)-5-oxo-1-phenyl-1,2,3,5-tetrahydroimidazo[1,2-a]pyrimidine-7-carboxamide White crystals; mp 199-200° C. (dichloromethane-ethyl acetate). (85% yield). $^1$HNMR 400 MHz (CDCl$_3$) δ (ppm): 4.22-4.31 (4H, m, 2×CH$_2$), 4.51 (2H, d, J=6.1 Hz, NCH$_2$), 5.19 (2H, s, OCH$_2$), 7.02 (2H, m, aromatics), 7.14-7.5 (10H, m, aromatics), 7.62 (1H, broad t, NH), 7.67-7.71 (2H, m, aromatics). HRMS (ESI$^+$) calculated for C$_{27}$H$_{24}$FN$_4$O$_3$ [M+H$^+$]: 471.1832. found: 471.1833.

EXAMPLE 20

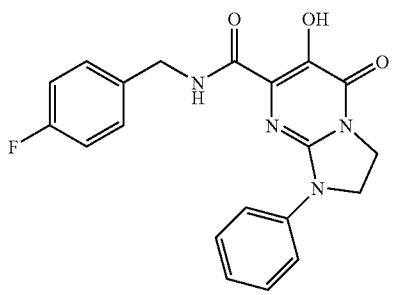

N-(4-Fluorobenzyl)-6-hydroxy-5-oxo-1-phenyl-1,2,3,5-tetrahydroimidazo[1,2-a]pyrimidine-7-carboxamide White crystals (dichloromethane-hexane). (81% yield). $^1$HNMR 400 MHz (CDCl$_3$) δ (ppm): 4.16 (2H, m, CH$_2$), 4.28 (2H, m, CH$_2$), 4.56 (2H, d, J=6.0 Hz, NCH$_2$), 7.05 (2H, m, aromatics), 7.15 (1H, m, aromatic), 7.30 (2H, m, aromatics), 7.37 (2H, m, aromatics), 7.50 (2H, m, aromatics), 7.72 (1H, broad t, NH),11.69 (1H, s, OH). HRMS (ESI$^+$) calculated for C$_{20}$H$_{18}$FN$_4$O$_3$ [M+H$^+$]: 381.1363. found: 381.1378.

Intermediate 35

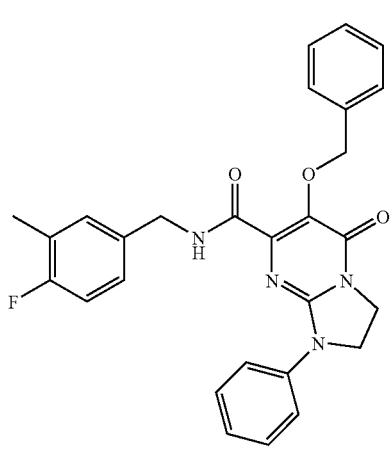

N-(4-Fluoro-3-methylbenzyl)-6-(benzyloxy)-5-oxo-1-phenyl-1,2,3,5-tetrahydroimidazo[1,2-a]pyrimidine-7-carboxamide White crystals; mp 147° C. (ethyl acetate). (86% yield). $^1$HNMR 400 MHz (DMSO-dr) δ (ppm): 2.12 (3H, s, CH$_3$), 4.12-4.25 (4H, m, 2×CH$_2$), 4.38 (2H, d, J=6.1 Hz, NCH$_2$), 4.97 (2H, s, OCH$_2$), 6.99 (1H, m, aromatic), 7.12-7.21 (3H, m, aromatics), 7.33-7.43 (7H, m, aromatics), 7.81 (2H, m, aromatics), 8.82 (1H, broad t, NH). HRMS (ESI$^+$) calculated for C$_{28}$H$_{26}$FN$_4$O$_3$ [M+H$^+$]: 485.1989. found: 485.1976.

EXAMPLE 21

Intermediate 36

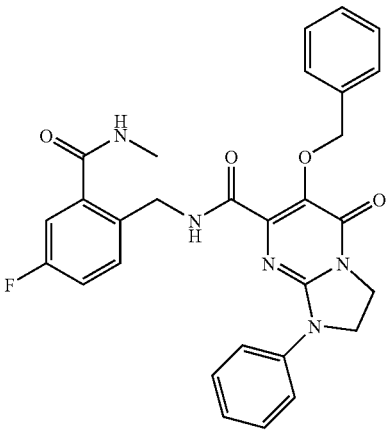

N-(4-Fluoro-2-(methylcarbamoyl)benzyl)-6-(benzyloxy)-5-oxo-1-phenyl-1,2,3,5-tetrahydroimidazo[1,2-a]pyrimidine-7-carboxamide White crystals; mp 194-195° C. (ethyl acetate). (76% yield). $^1$HNMR 400 MHz (DMSO-d$_6$) δ (ppm): 2.79 (3H, d, J=4.52 Hz, NCH$_3$), 4.14-4.25 (4H, m, 2×CH$_2$), 4.49 (2H, d, J=6.5 Hz, NCH$_2$), 5.0 (2H, s, OCH$_2$), 7.08 (1H, m, aromatic), 7.14 (1H, m, aromatic), 7.29 (1H, dd, J=2.7 Hz and J=9.3 Hz, aromatic), 7.33-7.45 (8H, m, aromatics), 7.82 (2H, m, aromatics), 8.52 (1H, broad q, NH), 8.80 (1H, broad t, NH). Anal. Calcd for C$_{29}$H$_{26}$FN$_5$O$_4$: C, 66.02; H, 4.96; N, 13.27. Found: C, 65.77; H, 5.19; N, 13.28.

EXAMPLE 22

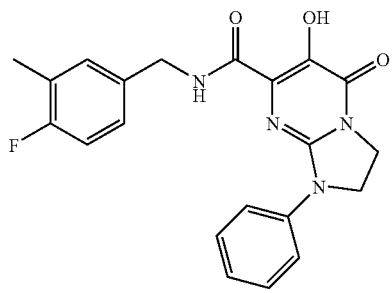

N-(4-Fluoro-3-methylbenzyl)-6-hydroxy-5-oxo-1-phenyl-1,2,3,5-tetrahydroimidazo[1,2-a]pyrimidine-7-carboxamide White crystals (ethyl acetate). (61% yield). $^1$HNMR 400 MHz (DMSO-d$_6$) δ (ppm): 2.22 (3H, s, CH$_3$), 4.14 (4H, broad s, 2×CH$_2$), 4.50 (2H, d, J=5.6 Hz, NCH$_2$), 7.11 (2H, m, aromatics), 7.20 (2H, m, aromatics), 7.4 (2H, m, aromatics), 7.8 (2H, m, aromatics), 8.83 (1H, broad t, NH), 12.06 (1H, s, OH). HRMS (ESI$^+$) calculated for C$_{21}$H$_{20}$FN$_4$O$_3$ [M+H$^+$]: 95.1519. found: 395.1521.

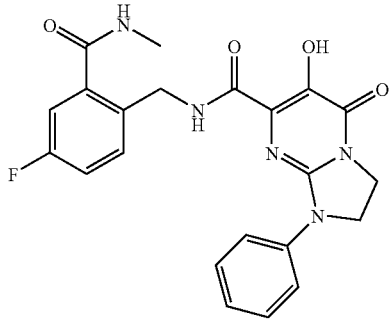

N-(4-Fluoro-2-(methylcarbamoyl)benzyl)-6-hydroxy-5-oxo-1-phenyl-1,2,3,5-tetrahydroimidazo[1,2-a]pyrimidine-7-carboxamide White crystals (ethyl acetate). (60% yield). $^1$HNMR 400 MHz (DMSO-d$_6$) δ (ppm): 2.88 (3H, d, J=4.5 Hz, NCH$_3$), 4.12 (4H, broad s, 2×CH$_2$), 4.54 (2H, d, J=6.6 Hz, NCH$_2$), 7.11 (1H, m, aromatic), 7.3-7.5 (5H, m, aromatics), 7.86 (2H, m, aromatics), 8.68 (H, broad q, NH), 9.18 (1H, broad, NH), 12.0 (11H, s, OH). HRMS (ESI$^+$) calculated for C$_{22}$H$_{21}$FN$_5$O$_4$ [M+H$^+$]: 438.1578. found: 438.1576.

Intermediate 37

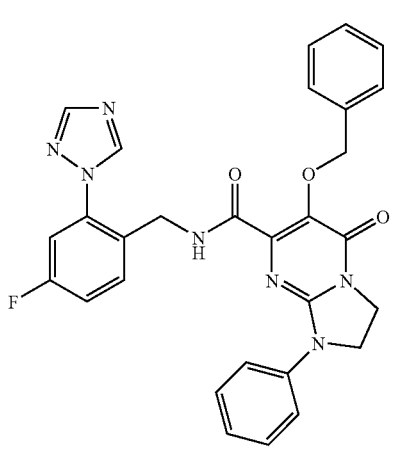

N-(4-Fluoro-2-(1H-1,2,4-triazol-1-yl)benzyl)-6-(benzyloxy)-5-oxo-1-phenyl-1,2,3,5-tetrahydroimidazo[1,2-a]pyrimidine-7-carboxamide White crystals; mp 187-190° C. (ethyl acetate). (74% yield). $^1$HNMR 400 MHz (DMSO-d$_6$) δ (ppm): 4.13-4.25 (4H, m, 2×CH$_2$), 4.33 (2H, d, J=6.08 Hz, NCH$_2$), 5.0 (2H, s, OCH$_2$), 7.11-7.17 (2H, m, aromatics), 7.32-7.43 (7H, m, aromatics), 7.47-7.58 (2H, m, aromatics), 7.76-7.81 (2H, m, aromatics), 8.29 (1H, s, CH), 8.80 (1H, broad t, NH), 9.0 (1H, s, CH). HRMS (ESI$^+$) calculated for C$_{29}$H$_{25}$FN$_7$O$_3$ [M+H$^+$]: 538.2003 found: 538.1993.

Intermediate 38

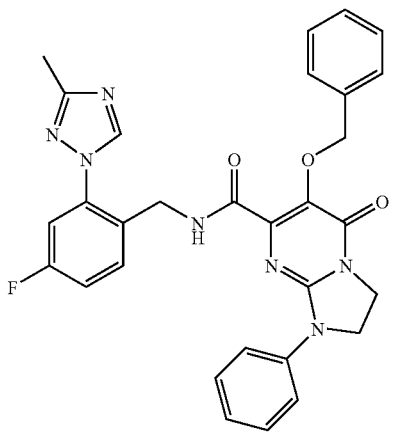

N-(4-Fluoro-2-(3-methyl-1H-1,2,4-triazol-1-yl)benzyl)-6-(benzyloxy)-5-oxo-1-phenyl-1,2,3,5-tetrahydroimidazo[1,2-a]pyrimidine-7-carboxamide White crystals; mp 147-148° C. (ethyl acetate). (84% yield). $^1$HNMR 400 MHz (CDCl$_3$) δ (ppm): 2.33 (3H, s, CH$_3$), 4.20-4.32 (4H, m, 2×CH$_2$), 4.46 (2H, d, J=6.5 Hz, NCH$_2$), 5.21 (2H, s, OCH$_2$), 7.07 (1H ,dd, J=2.5 Hz and J=8.6 Hz, aromatic), 7.10-7.18 (2H, m, aromatics), 7.27-7.35 (5H, m, aromatics), 7.42-7.46 (2H, m, aromatics), 7.69-7.73 (3H, m, aromatics), 8.26 (1H, s, CH), 8.29 (1H, broad t, NH). MS (ESI$^+$) m/e 552 [M+H$^+$].

EXAMPLE 23

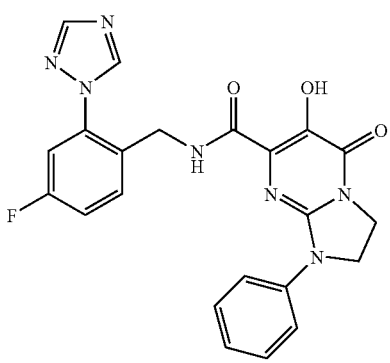

N-(4-Fluoro-2-(1H-1,2,4-triazol-1-yl)benzyl)-6-hydroxy-5-oxo-1-phenyl-1,2,3,5-tetrahydroimidazo[1,2-a]pyrimidine-7-carboxamide White crystals (dichloromethane-ethanol). (53% yield). $^1$HNMR 400 MHz (DMSO-d$_6$) δ (ppm): 4.13 (4H, s, 2×CH$_2$), 4.46 (2H, d, J=6.1 Hz, NCH$_2$), 711 (1H, m, aromatic), 7.34-7.45 (3H, m, aromatics), 7.61 (2H, m, aromatics), 7.77 (2H, m, aromatics), 8.29 (1H, s, CH), 8.81 (1H, broad t, NH), 9.09 (1H, s, CH), 11.89 (1H, s, OH). HRMS (ESI$^+$) calculated for C$_{22}$H$_{19}$FN$_7$O$_3$ [M+H$^+$]: 448.1533. found: 448.1550.

EXAMPLE 24

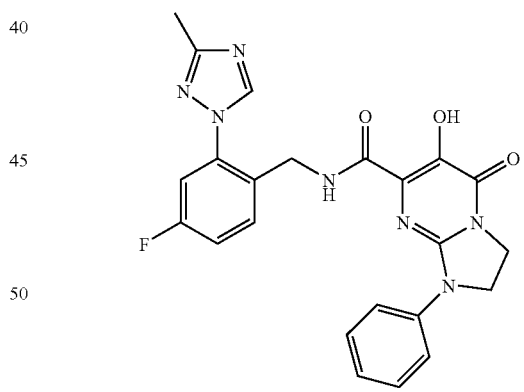

N-(4-Fluoro-2-(3-methyl-1H-1,2,4-triazol-1-yl)benzyl)-6-hydroxy-5-oxo-1-phenyl-1,2,3,5-tetrahydroimidazo[1,2-a]pyrimidine-7-carboxamide White crystals (ethyl acetate). (71% yield). $^1$HNMR 400 MHz (CDCl$_3$) δ (ppm): 2.23 (3H, s, CH$_3$), 4.18 (2H, m, CH$_2$), 4.29 (2H, m, CH$_2$), 4.49 (2H, d, J=6.6 Hz, NCH$_2$), 7.09-7.15 (2H, m, aromatics), 7.18-7.23 (1H, m, aromatic), 7.28-7.32 (2H, m, aromatics), 7.6-7.7 (3H, m, aromatics), 8.33 (1H, s, CH), 8.62 (1H, broad t, NH), 11.91 (1H, s, OH). MS (ESI$^+$) m/e 462 [M+H$^+$].

Intermediate 39

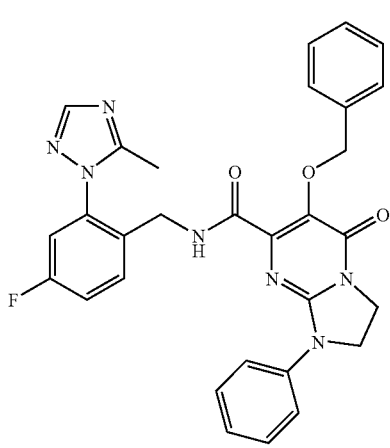

N-(4-Fluoro-2-(5-methyl-1H-1,2,4-triazol-1-yl)benzyl)-6-(benzyloxy)-5-oxo-1-phenyl-1,2,3,5-tetrahydroimidazo[1,2-a]pyrimidine-7-carboxamide White crystals; mp 181° C. (ethyl acetate). (72% yield). $^1$HNMR 400 MHz (CDCl$_3$) δ (ppm): 2.44 (3H, s, CH$_3$), 4.23-4.32 (6H, m, 2×CH$_2$ and NCH$_2$), 5.22 (2H, s, OCH$_2$), 7.00 (1H, dd, J=2.7 Hz and J=8.5 Hz, aromatic), 7.16-7.22 (2H, m, aromatics), 7.28-7.33 (3H, m, aromatics), 7.39-7.43 (2H, m, aromatics), 7.49-7.51 (2H, m, aromatics), 7.69-7.73 (3H, m, aromatics), 7.81 (1H, s, CH), 8.05 (1H, broad t, NH). Anal. Calcd for C$_{30}$H$_{26}$FN$_7$O$_3$: C, 65.32; H, 4.75; N, 17.77. Found: C, 65.03; H, 4.56; N, 17.49.

EXAMPLE 25

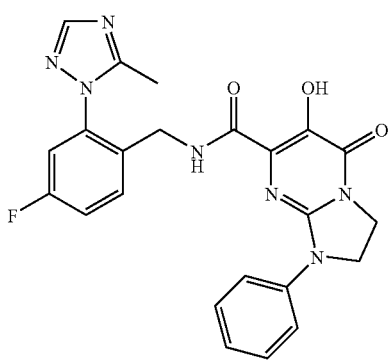

N-(4-Fluoro-2-(5-methyl-1H-1,2,4-triazol-1-yl)benzyl)-6-hydroxy-5-oxo-1-phenyl-1,2,3,5-tetrahydroimidazo[1,2-a]pyrimidine-7-carboxamide White crystals (65% yield). $^1$HNMR 400 MHz (CDCl$_3$) δ (ppm): 2.50 (3H, s, CH$_3$), 4.19 (2H, m, CH$_2$), 4.28 (4H, m, 2×CH$_2$), 7.04 (1H, dd, J=2.5 Hz and J=8.3 Hz, aromatic), 7.15-7.27 (2H, m, aromatics), 7.44 (2H, m, aromatics), 7.65-7.75 (2H, m, aromatics), 7.90 (1H, s, CH), 8.42 (1H, broad t, NH), 11.87 (1H, s, OH). MS (ESI$^+$) m/e 462 [M+H$^+$].

Intermediate 40

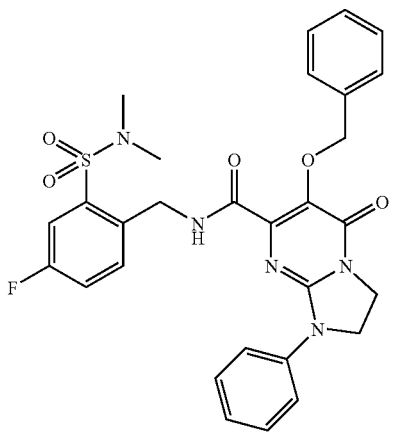

N-(4-Fluoro-2-(N,N-dimethylsulfamoyl)benzyl)-6-hydroxy-5-oxo-1-phenyl-1,2,3,5-tetrahydroimidazo[1,2-a]pyrimidine-7-carboxamide White crystals (acetonitrile). (75% yield). $^1$HNMR 400 MHz (DMSO-d$_6$) δ (ppm): 2.80 (6H, s, 2×NCH$_3$), 4.16-4.26 (4H, m, 2×CH$_2$), 4.72 (2H, d, J=6.4 Hz, NCH$_2$), 5.03 (2H, s, OCH$_2$), 7.13-7.23 (2H, m, aromatics), 7.32-7.46 (7H, m, aromatics), 7.57-7.63 (2H, m, aromatics), 7.80-7.82 (2H, m, aromatics), 8.83 (1H, broad t, NH). HRMS (ESI$^+$) calculated for C$_{29}$H$_{29}$FN$_5$O$_5$S [M+H$^+$]: 578.1873. found: 578.1852.

EXAMPLE 26

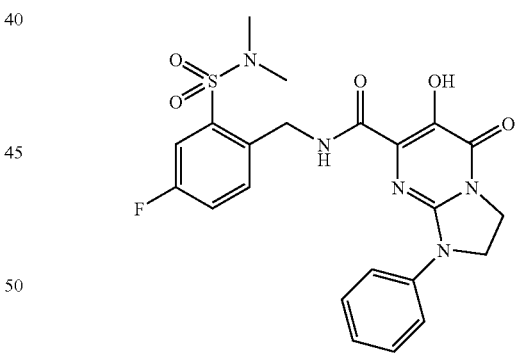

N-(4-Fluoro-2-(N,N-dimethylsulfamoyl)benzyl)-6-hydroxy-5-oxo-1-phenyl-1,2,3,5-tetrahydroimidazo[1,2-a]pyrimidine-7-carboxamide White crystals (ethyl acetate). (90% yield). $^1$HNMR 400 MHz (DMSO-d$_6$) δ (ppm): 2.85 (6H, s, 2×NCH$_3$), 4.13 (4H, s, 2×CH$_2$), 4.82 (2H, d, J=6.6 Hz, NCH$_2$), 7.11 (1H, m, aromatic), 7.42 (2H, m, aromatics), 7.55-7.65 (3H, m, aromatics), 7.78 (2H, m, aromatics), 8.77 (1H, broad t, NH), 11.76 (1H, s, OH). HRMS (ESI$^+$) calculated for C$_{22}$H$_{23}$FN$_5$O$_5$S [M+H$^+$]: 488.1404. found: 488.1419.

Intermediate 41

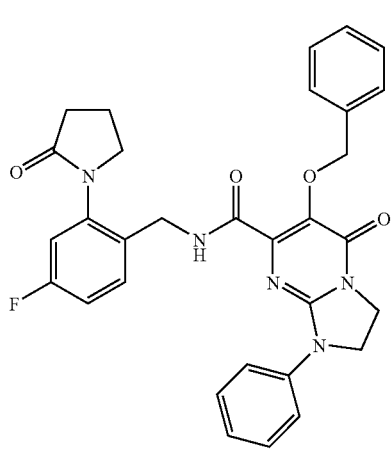

N-(4-Fluoro-2-(2-oxopyrrolidin-1-yl)benzyl)-6-(benzyloxy)-5-oxo-1-phenyl-1,2,3,5-tetrahydroimidazo[1,2-a]pyrimidine-7-carboxamide White crystals (ethyl acetate). (58% yield). $^1$HNMR 400 MHz (CDCl$_3$) δ (ppm): 2.23 (2H, m, CH$_2$), 2.58 (2H, t, J=8.0 Hz, CH$_2$), 3.79 (2H, t, J=7.0 Hz, CH$_2$), 4.15-4.30 (4H, m, 2×CH$_2$), 4.46 (2H, d, J=6.0 Hz, NCH$_2$), 5.22 (2H, s, OCH$_2$), 6.91 (1H, dd, J=2.6 Hz and J=9.4 Hz, aromatic), 6.99 (1H, m, aromatic), 7.14 (1H, m, aromatic), 7.30-7.46 (5H, m, aromatics), 7.44 (1H, dd, J=6.1 Hz and J=8.6 Hz, aromatic), 7.50-7.52 (2H, m, aromatics), 7.69-7.71 (2H, m, aromatics), 7.95 (1H, broad t, NH). MS (ESI$^+$) m/e 554 [M+H$^+$].

Intermediate 42

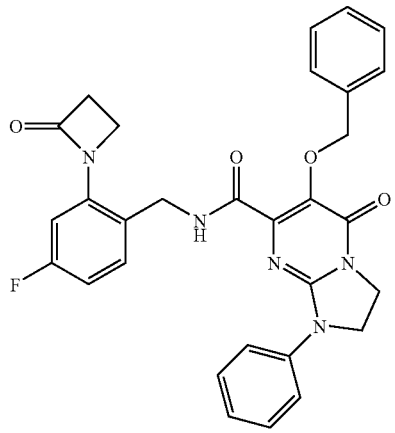

N-(4-Fluoro-2-(2-oxoazetidin-1-yl)benzyl)-6-(benzyloxy)-5-oxo-1-phenyl-1,2,3,5-tetrahydroimidazo[1,2-a]pyrimidine-7-carboxamide White crystals (ethyl acetate). (22% yield). $^1$HNMR 400 MHz (CDCl$_3$) δ (ppm): 3.10 (2H, t, J=4.4 Hz, CH$_2$), 3.73 (2H, t, J=4.4 Hz, CH$_2$), 4.19-4.31 (4H, m, 2×CH$_2$), 4.60 (2H, d, J=6.3 Hz, NCH$_2$), 5.21 (2H, s, OCH$_2$), 6.88 (1H, m, aromatic), 6.93 (1H, dd, J=2.4 Hz and J=9.7 Hz, aromatic), 7.16 (1H, m, aromatic), 7.29-7.31 (3H, m, aromatics), 7.39-7.43 (2H, m, aromatics), 7.47-7.48 (2H, m, aromatics), 7.54 (1H, dd, J=6.3 Hz and J=8.3 Hz, aromatic), 7.70-7.72 (2H, m, aromatics), 8.25 (1H, broad t, NH). MS (ESI$^+$) m/e 540 [M+H$^+$].

EXAMPLE 27

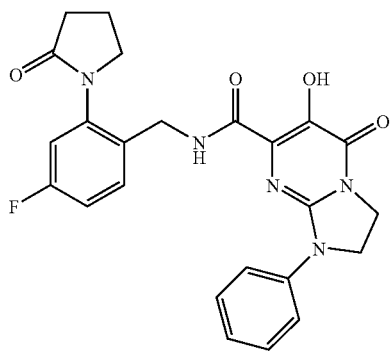

N-(4-Fluoro-2-(2-oxopyrrolidin-1-yl)benzyl)-6-hydroxy-5-oxo-1-phenyl-1,2,3,5-tetrahydroimidazo[1,2-a]pyrimidine-7-carboxamide White crystals (78% yield). $^1$HNMR 400 MHz (DMSO-d$_6$) δ (ppm): 2.15 (2H, m, CH$_2$), 2.55 (2H, t, J=7.9 Hz, CH$_2$), 3.81 (2H, t, J=6.9 Hz, CH$_2$), 4.13 (4H, broad s, 2×CH$_2$), 4.41 (2H, d, J=6.4 Hz, NCH$_2$), 7.07 (1H, m, aromatic), 7.18 (1H, m, aromatic), 7.28 (1H, dd, J=2.5 Hz and J=10 Hz, aromatic), 7.36-7.40 (2H, m, aromatics), 7.45 (1H, dd, J=6.5 Hz and J=8.6 Hz, aromatic), 7.82-7.84 (2H, m, aromatics), 8.87 (1H, broad t, NH), 12.10 (1H, s, OH). MS (ESI$^+$) m/e 464 [M+H$^+$].

EXAMPLE 28

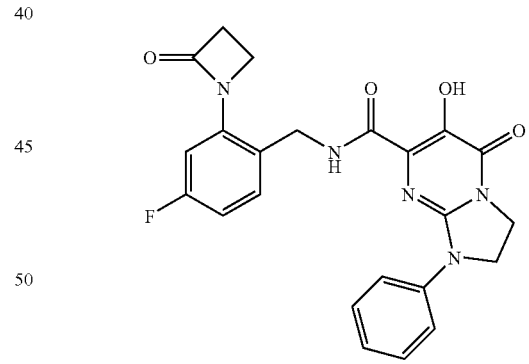

N-(4-Fluoro-2-(2-oxoazetidin-1-yl)benzyl)-6-hydroxy-5-oxo-1-phenyl-1,2,3,5-tetrahydroimidazo[1,2-a]pyrimidine-7-carboxamide White crystals (dichloromethane). (67% yield). $^1$HNMR 400 MHz (DMSO-d$_6$) δ (ppm): 3.17 (2H, t, J=4.4 Hz, CH$_2$), 3.82 (2H, t, J=4.4 Hz, CH$_2$), 4.13 (4H, broad s, 2×CH$_2$), 4.59 (2H, d, J=6.6 Hz, NCH$_2$), 7.07-7.11 (2H, m, aromatics), 7.23 (1H, dd, J=2.5 Hz and J=10.4 Hz, aromatic), 7.37-7.41 (2H, m, aromatics), 7.45 (1H, dd, J=6.6 Hz and J=8.6 Hz, aromatic), 7.82-7.84 (2H, m, aromatics), 9.04 (1H, broad t, NH), 12.03 (1H, s, OH). MS (ESI$^+$) m/e 450 [M+H$^+$].

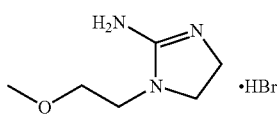

Intermediate 43

1-(2-Methoxyethyl)-4,5-dihydro-1H-imidazol-2-amine hydrobromide

Reaction of N-(2-methoxyethyl)ethylenediamine (16.0 g, 0.135 mol) (R. C. F. Jones and J. R. Nichols, Tetrahedron Lett., 1990, 31, 1767-1770) with cyanogen bromide (14.34 g, 0.135 mol) as described in the preparation of intermediate 6 gave 26.86 g (88% yield) of the title product as large white prisms (ethanol); mp 143-145° C.

$^1$HNMR 400. $^1$HNMR 400 MHz (DMSO-$d_6$) δ (ppm): 3.28 (3H, s, OCH$_3$), 3.48 (4H, s, 2×CH$_2$), 3.52 (2H, m, CH$_2$), 3.67 (2H, m, CH$_2$), 7.87 (broad s, NH). Anal. Calcd for C$_6$H$_{13}$N$_3$O.HBr: C, 32.15; H, 6.29; N, 18.75. Found: C, 32.23; H, 6.14; N, 18.85.

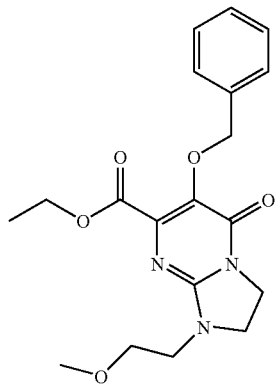

Intermediate 44

Ethyl 6-(benzyloxy)-1-(2-methoxyethyl)-5-oxo-1,2,3,5-tetrahydroimidazo[1,2-a]pyrimidine-7-carboxylate Reaction of the adduct of diethyl oxalate (16.95 g, 0.116 mol), ethyl benzyloxyacetate (22.53 g, 0.116 mol) and sodium hydride (5.10 g of a 60% dispersion in mineral oil, 0.127 mol) with 1-(2-methoxyethyl)-4,5-dihydro-1H-imidazol-2-amine hydrobromide (26.0 g, 0.116 mol) as described for intermediate 1 gave 5.37 g (12% yield) of the title ester as a clear oil. $^1$HNMR 400 MHz (CDCl$_3$) δ (ppm): 1.31 (3H, t, J=7.1 Hz, CH$_3$), 3.38 (3H, s, OCH$_3$), 3.61 (4H, s, 2×CH$_2$), 3.84 (2H, t, J=8.9 Hz, CH$_2$), 4.14 (2H, t, J=8.9 Hz, CH$_2$), 4.32 (2H, q, J=7.1 Hz, OCH$_2$), 5.09 (2H, s, OCH$_2$), 7.3-7.38 (3H, m, aromatics), 7.49 (2H, m, aromatics). MS (ESI$^+$) m/e 374 [M+H$^+$].

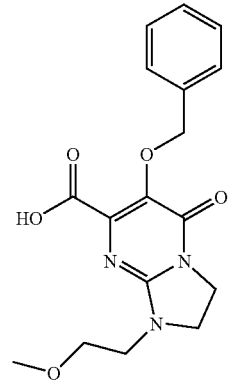

Intermediate 45

6-(Benzyloxy)-1-(2-methoxyethyl)-5-oxo-1,2,3,5-tetrahydroimidazo[1,2-a]pyrimidine-7-carboxylic acid White crystals; mp 125-126° C. (ethyl acetate). (97% yield). $^1$HNMR 400 MHz (CDCl$_3$) δ (ppm): 3.38 (3H, s, OCH$_3$), 3.61 (4H, s, 2×CH$_2$), 3.86 (2H, t, J=9.0 Hz, CH$_2$), 4.16 (2H, t, J=9.0 Hz, CH$_2$), 5.26 (2H, s, OCH$_2$), 7.35-7.40 (3H, m, aromatics), 7.57 (2H, m, aromatics). Anal. Calcd for C$_{17}$H$_{19}$N$_3$O$_5$: C, 59.12; H, 5.54; N, 12.16. Found: C, 59.04; H, 5.55; N, 12.10.

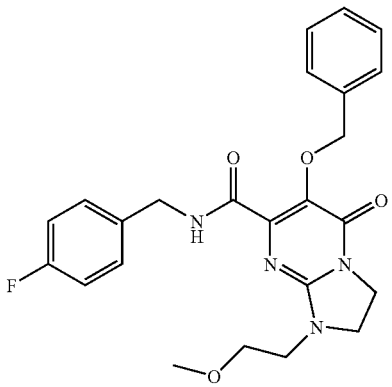

Intermediate 46

N-(4-Fluorobenzyl)-6-(benzyloxy)-1-(2-methoxyethyl)-5-oxo-1,2,3,5-tetrahydroimidazo[1,2-a]pyrimidine-7-carboxamide White crystals; mp 150° C. (ethyl acetate). (79% yield). $^1$HNMR 400 MHz (CDCl$_3$) δ (ppm): 3.38 (3H, s, OCH$_3$), 3.61 (4H, s, 2×CH$_2$), 3.84 (2H, t, J=8.9 Hz, CH$_2$), 4.14 (2H, t, J=8.9 Hz, CH$_2$), 4.49 (2H, d, J=6.1 Hz, NCH$_2$), 5.10 (2H, s, OCH$_2$), 6.99 (2H, m, aromatics), 7.24 (2H, m, aromatics), 7.33-7.36 (3H, m, aromatics), 7.43-7.45 (2H, m, aromatics), 7.67 (1H, broad t, NH). Anal. Calcd for $C_{24}H_{25}FN_4O_4$: C, 63.70; H, 5.56; N, 12.38; Found: C, 64.00; H, 5.41; N, 12.10.

EXAMPLE 29

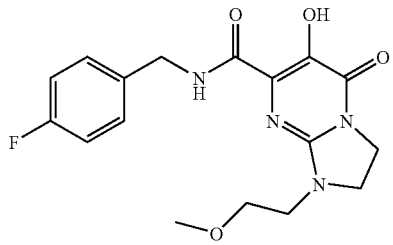

N-(4-Fluorobenzyl)-6-hydroxy-1-(2-methoxyethyl)-5-oxo-1,2,3,5-tetrahydroimidazo[1,2-a]pyrimidine-7-carboxamide White crystals; mp 166° C. (ethanol). (96% yield). $^1$HNMR 400 MHz (CDCl$_3$) δ (ppm): 3.38 (3H, s, OCH$_3$), 3.51 (2H, m, CH$_2$), 3.59 (2H, m, CH$_2$), 3.76 (2H, t, J=8.6 Hz, CH$_2$), 4.14 (2H, t, J=8.6 Hz, CH$_2$), 4.58 (2H, d, J=6.6 Hz, NCH$_2$), 7.07 (2H, m, aromatics), 7.32 (2H, m, aromatics), 7.85 (1H, broad t, NH), 11.57 (1H, s, OH). Anal. Calcd for $C_{17}H_{19}FN_4O_4$: C, 56.34; H, 5.28; N, 15.46. Found: C, 56.39; H, 5.37; N, 15.27.

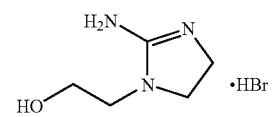

Intermediate 47

1-(2-Hydroxyethyl)-4,5-dihydro-1H-imidazol-2-amine hydrobromide

Reaction of 2-(2-aminoethylamino)ethanol (8.0 g, 76.8 mmol) with cyanogen bromide (8.13 g, 76.8 mmol) as described in the preparation of intermediate 6 gave 13.27 g (82% yield) of the title product as large white prisms (ethanol); mp 112-115° C. $^1$HNMR 400.$^1$HNMR 400 MHz (DMSO-d$_6$) δ (ppm): 3.36 (2H, t, J=5.3 Hz, CH$_2$), 3.50-3.58 (4H, m, 2×CH$_2$), 3.69 (2H, m, CH$_2$), 4.97 (1H, t, J=5.0 Hz, OH), 7.73 and 7.85 (broad s, NH). Anal. Calcd for $C_5H_{11}N_3O\cdot HBr$: C, 28.58; H, 5.75, N 20.00. Found: C, 28.79; H, 5.58; N, 20.12.

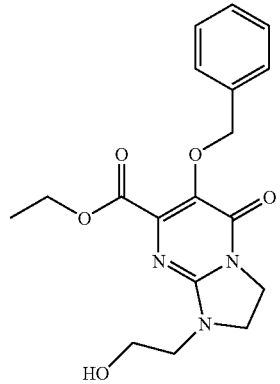

Intermediate 48

Ethyl 6-(benzyloxy)-1-(2-hydroxyethyl)-5-oxo-1,2,3,5-tetrahydroimidazo[1,2-a]pyrimidine-7-carboxylate Reaction of the adduct of diethyl oxalate (14.61 g, 0.10 mol), ethyl benzyloxyacetate (19.42 g, 0.10 mol) and sodium hydride (4.40 g of a 60% dispersion in mineral oil, 0.11 mol) with 1-(2-hydroxyethyl)-4,5-dihydro-1H-imidazol-2-amine hydrobromide (21.0 g, 0.10 mol) as described for intermediate 1 gave 3.37 g (9% yield) of the title ester as white crystals; mp 104-106° C. (ethyl acetate-hexane). $^1$HNMR 400 MHz (CDCl$_3$) δ (ppm): 1.32 (3H, t, J=7.1 Hz, CH$_3$), 3.53 (2H, m, CH$_2$), 3.83 (2H, t, J=8.9 Hz, CH$_2$), 3.90 (2H, m, CH$_2$), 4.19 (2H, t, J=8.9 Hz, CH$_2$), 4.32 (2H, q, J=7.1 Hz, OCH$_2$), 5.11 (2H, s, OCH$_2$), 7.35-7.40 (3H, m, aromatics), 7.51 (2H, m, aromatics). Anal. Calcd for $C_{18}H_{21}N_3O_5$: C, 60.16; H, 5.89, N 11.69. Found: C, 60.24; H, 5.89, N, 11.77.

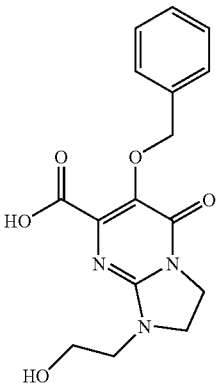

Intermediate 49

6-(Benzyloxy)-1-(2-hydroxyethyl)-5-oxo-1,2,3,5-tetrahydroimidazo[1,2-a]pyrimidine-7-carboxylic acid White crystals (ethyl acetate). (80% yield). $^1$HNMR 400 MHz (DMSO-d$_6$) δ (ppm): 3.36 (2H, t, J=5.8 Hz, CH$_2$), 3.58 (2H, broad t, CH$_2$), 3.76 (2H, t, J=9.1 Hz, CH$_2$), 4.02 (2H, t, J=9.1 Hz, CH$_2$), 4.85 (1H, broad, OH), 4.90 (2H, s, OCH$_2$), 7.34-7.43 (5H, m, aromatics), 13.3 (H, broad, OH). MS (ESI$^+$) m/e 332 [M+H$^+$].

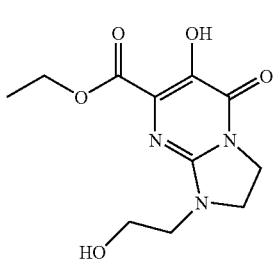

Intermediate 50

Ethyl 6-hydroxy-1-(2-hydroxyethyl)-5-oxo-1,2,3,5-tetrahydroimidazo[1,2-a]pyrimidine-7-carboxylate A solution of ethyl 6-(benzyloxy)-1-(2-hydroxyethyl)-5-oxo-1,2,3,5-tetrahydroimidazo[1,2-a]pyrimidine-7-carboxylate (1.40 g, 3.89 mmol) in a mixture of ethyl acetate (300 ml) and ethanol (75 ml) at 25° C. was hydrogenated over 10% palladium on activated carbon (200 mg) and under one atmosphere of hydrogen for four hours to give 1.05 g (100% yield) of the title compound as light yellow needles; mp 155-156° C. (ethyl acetate). $^1$HNMR 400 MHz (CDCl$_3$) δ (ppm): 1.44 (3H, t, J=7.1 Hz, CH$_3$), 3.46 (2H, m, CH$_2$), 3.75 (2H, t, J=8.3 Hz, CH$_2$), 3.92 (2H, m, CH$_2$), 4.20 (2H, t, J=8.3 Hz, CH$_2$), 4.43 (2H, q, J=7.1 Hz, OCH$_2$), 10.20 (1H, s, OH). Anal. Calcd for C$_{11}$H$_{15}$N$_3$O$_5$: C, 49.06; H, 5.61; N, 15.60. Found: C, 49.09, H, 5.73; N, 15.58.

EXAMPLE 30

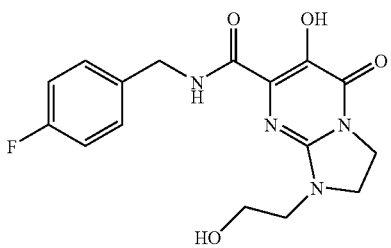

N-(4-Fluorobenzyl)-6-hydroxy-1-(2-hydroxyethyl)-5-oxo-1,2,3,5-tetrahydroimidazo[1,2-a]pyrimidine-7-carboxamide A solution of ethyl 6-hydroxy-1-(2-hydroxyethyl)-5-oxo-1,2,3,5-tetrahydroimidazo[1,2-a]pyrimidine-7-carboxylate (0.110 g, 0.408 mmol) and 4-fluorobenzylamine (0.200 g, 1.6 mmol) in anhydrous ethanol (5 ml) was heated under reflux for 6 h. The reaction mixture was then diluted with ethyl acetate, washed successively with 0.1 N hydrochloric acid and brine, dried over anhydrous magnesium sulfate and concentrated under reduced pressure. Crystallization of the residual solid from ethanol gave 0.116 g (82% yield) of the title amide as white cubes; mp 203° C. $^1$HNMR 400 MHz (CDCl$_3$) δ (ppm): 3.54 (2H, t, J=5.0 Hz, CH$_2$), 3.80 (2H, t, J=8.5 Hz, CH$_2$), 3.89 (2H, t, J=5.0 Hz, CH$_2$), 4.15 (2H, t, J=8.5 Hz, CH$_2$), 4.57 (2H, d, J=6.0 Hz, NCH$_2$), 7.07 (2H, m, aromatics), 7.34 (2H, m, aromatics), 7.92 (1H, broad t, NH), 11.68 (1H, s, OH). Anal. Calcd for C$_{16}$H$_{17}$FN$_4$O$_4$: C, 55.17; H, 4.92; N, 16.08. Found: C, 55.22; H, 5.06; N, 15.89.

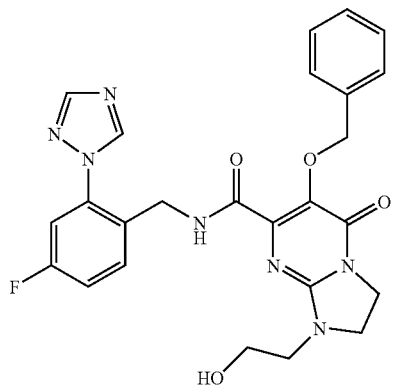

Intermediate 51

N-(4-Fluoro-2-(1H-1,2,4-triazol-1-yl)benzyl)-6-(benzyloxy)-1-(2-hydroxyethyl)-5-oxo-1,2,3,5-tetrahydroimidazo[1,2-a]pyrimidine-7-carboxamide White solid (67% yield). $^1$HNMR 400 MHz (CDCl$_3$) δ (ppm): 3.55 (2H, t, J=5.0 Hz, CH$_2$), 3.81 (2H, t, J=8.7 Hz, CH$_2$), 3.88 (2H, t, J=5.0 Hz, CH$_2$), 4.17 (2H, t, J=8.7 Hz, CH$_2$), 4.42 (2H, d, J=6.1 Hz, NCH$_2$), 5.13 (2H, s, OCH$_2$), 7.06 (1H, dd, J=2.5 Hz and J=8.6 Hz, aromatic), 7.18 (1H, m, aromatic), 7.25-7.31 (3H, m, aromatics), 7.39-7.41 (2H, m, aromatics), 7.69 (1H, dd, J=5.5 Hz and J=8.6 Hz, aromatic), 7.98 (1H, s, CH), 8.27 (1H, broad t, NH), 8.38 (1H, s, CH). MS (ESI$^+$) m/e 506 [M+H$^+$].

EXAMPLE 31

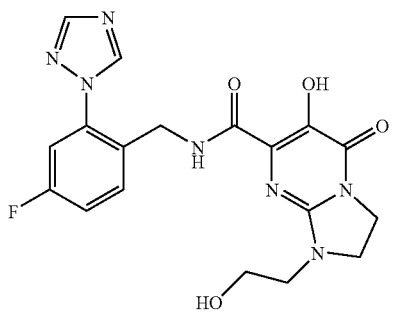

N-(4-Fluoro-2-(1H-1,2,4-triazol-1-yl)benzyl)-6-hydroxy-(2-hydroxyethyl)-5-oxo-1,2,3,5-tetrahydroimidazo[1,2-a]pyrimidine-7-carboxamide White crystals; mp 220-222° C. (ethanol). (86% yield). $^1$HNMR 400 MHz (DMSO-d$_6$) δ (ppm): 3.42 (2H, t, J=5.8 Hz, CH$_2$), 3.62 (2H, m, CH$_2$), 3.68 (2H, t, J=8.5 Hz, CH$_2$), 3.98 (2H, t, J=8.5 Hz, CH$_2$), 4.41 (2H, d, J=6.0 Hz, NCH$_2$), 4.79 (1H, t, J=5.6 Hz, OH), 7.42 (1H, m, aromatic), 7.53 (1H, dd, J=6.1 Hz and J=8.6 Hz, aromatic), 7.57 (1H, dd, J=2.7 Hz and J=9.3 Hz, aromatic), 8.34 (1H, s, CH), 9.06 (1H, s, CH), 9.16 (1H, broad t, NH), 11.43 (1H, s, OH). MS (ESI$^+$) m/e 416 [M+H$^+$].

Some other examples of formula I compounds are listed in table 4.

TABLE 4

| Example | Structure |
|---------|-----------|
| 32 | 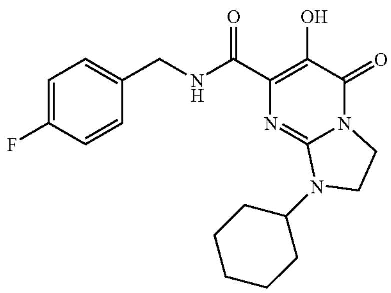 |
| 33 | 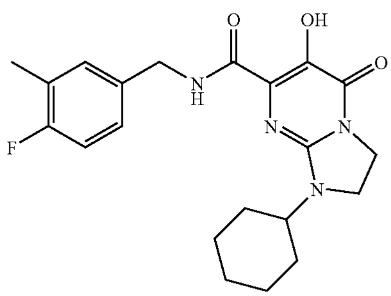 |
| 34 | 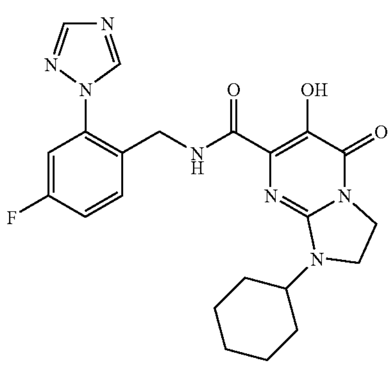 |
| 35 | 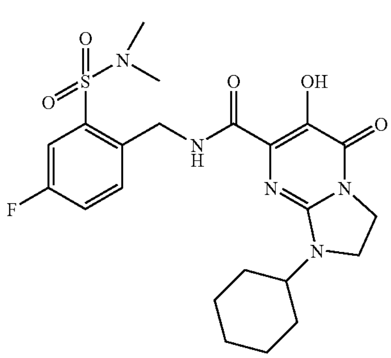 |

TABLE 4-continued

| Example | Structure |
|---------|-----------|
| 36 | 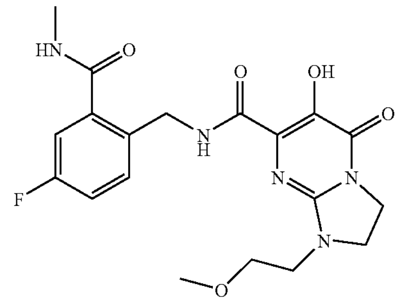 |
| 37 | 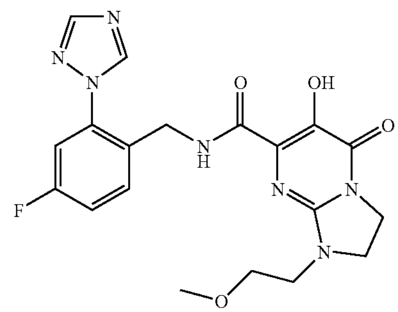 |
| 38 | 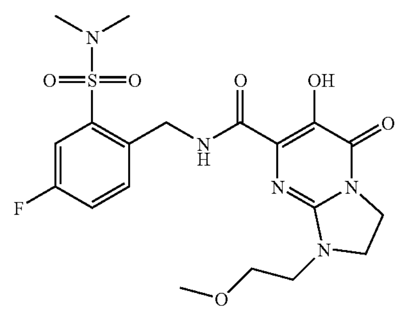 |
| 39 | 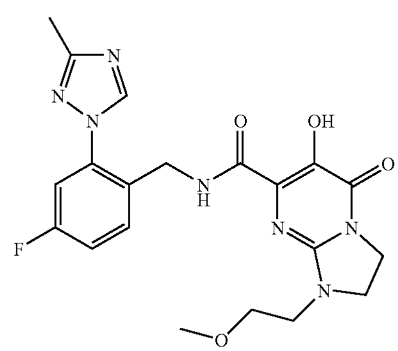 |
| 40 | 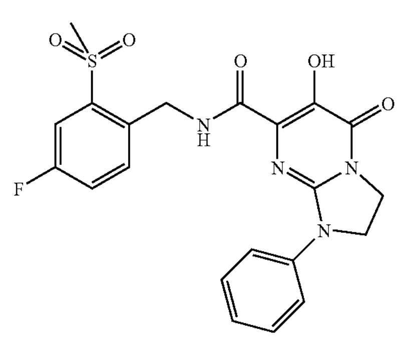 |

TABLE 4-continued

| Example | Structure |
|---------|-----------|
| 41 | 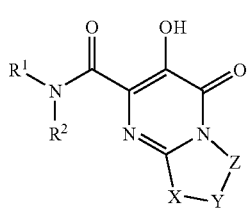 |
| 42 | 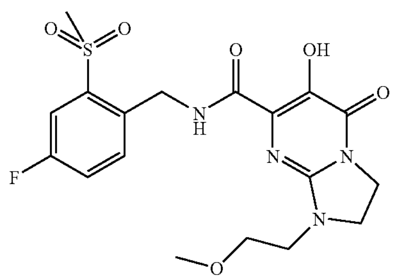 |
| 43 | 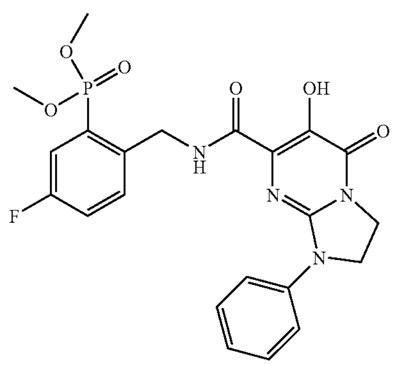 |

We claim:

1. A compound of Formula I

I wherein:
R¹ is (Ar¹)alkyl;
R² is hydrogen, hydroxy, alkyl, or alkoxy;
R³ is hydrogen, halo, hydroxy, cyano, alkyl, haloalkyl, alkoxy, haloalkoxy, $C_{4-6}$lactamyl, N(R⁶)SO₂R⁷, N(R⁶)COR⁷, N(R⁶)CO₂R⁷, OCOR⁷, OCO₂R⁷, OCON(R⁶)(R⁶), COR⁷, CO₂R⁶, CON(R⁶)(R⁶), SOR⁷, SO₂R⁷, SO₂N(R⁶)(R⁶), P(O)(OR⁶)₂, or Ar²;
R⁴ is hydrogen, halo, hydroxy, cyano, alkyl, alkoxy, haloalkyl, or haloalkoxy;

R⁵ is hydrogen, halo, hydroxy, cyano, alkyl, alkoxy, haloalkyl, or haloalkoxy;
R⁶ is hydrogen, alkyl, or cycloalkyl;
R⁷ is alkyl or cycloalkyl;
R⁸ is hydrogen or alkyl;
R⁹ is hydrogen, alkyl, cycloalkyl, hydroxyalkyl, (alkoxy)alkyl, phenyl, or benzyl, wherein phenyl and benzyl are substituted with 0-2 substituents selected from the group consisting of halo, cyano, alkyl, alkoxy, halolkyl, and haloalkoxy;
Ar¹ is Ar² is tetrazolyl, triazolyl, pyrazolyl, imidazolyl, pyrrolyl, or dioxothiazinyl, and is substituted with 0-2 substituents selected from the group consisting of amino, oxo, halo, and alkyl; and
X—Y-Z is N(R⁹)C(R⁸)₂C(R⁸)₂;
or a pharmaceutically acceptable salt thereof.

2. A compound of claim 1 where R¹ is

3. A compound of claim 1 where R¹ is provided that R³ is not hydrogen.

4. A compound of claim 1 where R¹ is and R³ is $C_{4-6}$lactamyl, N(R⁶)SO₂R⁷, N(R⁶)COR⁷, N(R⁶)CO₂R⁷, OCOR⁷, OCO₂R⁷, OCON(R⁶)(R⁶), COR⁷, CO₂R⁶, CON(R⁶)(R⁶), SOR⁷, SO₂R⁷, SO₂N(R⁶)(R⁶), or Ar².

5. A compound of claim 1 where R² is hydrogen.

6. A compound of claim 1 where R³ is triazolyl substituted with 0-1 methyl groups; R⁴ is hydrogen, chloro, flouro, or methyl; and R⁵ is hydrogen.

7. A compound of claim 1 where R⁶ is hydrogen or alkyl.

8. A compound of claim 1 where R⁷ is alkyl.

9. A compound of claim 1 where X—Y-Z is N($R^9$)$CH_2CH_2$.

10. A compound of claim 1 where $R^9$ is alkyl, cycloalkyl, hydroxyalkyl, (alkoxy)alkyl, phenyl, or benzyl.

11. A compound selected from the group consisting of
N-[(4-fluorophenyl)methyl]-1,2,3,5-tetrahydro-6-hydroxy-1-methyl-5-oxo-imidazo[1,2-a]pyrimidine-7-carboxamide;
N-[(4-fluoro-3-methylphenyl)methyl]-1,2,3,5-tetrahydro-6-hydroxy-1-methyl-5-oxo-imidazo[1,2-a]pyrimidine-7-carboxamide;
N-[[4-fluoro-2-[(methylamino)carbonyl]phenyl]methyl]-1,2,3,5-tetrahydro-6-hydroxy-1-methyl-5-oxo-imidazo[1,2-a]pyrimidine-7-carboxamide;
N-[(4-fluorophenyl)methyl]-1,2,3,5-tetrahydro-6-hydroxy-5-oxo-1-(phenylmethyl)-imidazo[1,2-a]pyrimidine-7-carboxamide;
N-[(4-fluoro-3-methylphenyl)methyl]-1,2,3,5-tetrahydro-6-hydroxy-5-oxo-1-(phenylmethyl)-imidazo[1,2-a]pyrimidine-7-carboxamide;
N-[[4-fluoro-2-[(methylamino)carbonyl]phenyl]methyl]-1,2,3,5-tetrahydro-6-hydroxy-5-oxo-1-(phenylmethyl)-imidazo[1,2-a]pyrimidine-7-carboxamide;
N-[(4-fluorophenyl)methyl]-1,2,3,5-tetrahydro-6-hydroxy-5-oxo-1-phenyl-imidazo[1,2-a]pyrimidine-7-carboxamide;
N-[[4-fluoro-2-(1H-1,2,4-triazol-1-yl)phenyl]methyl]-1,2,3,5-tetrahydro-6-hydroxy-5-oxo-1-(phenylmethyl)-imidazo[1,2-a]pyrimidine-7-carboxamide;
N-[(4-fluoro-3-methylphenyl)methyl]-1,2,3,5-tetrahydro-6-hydroxy-5-oxo-1-phenyl-imidazo[1,2-a]pyrimidine-7-carboxamide;
N-[[4-fluoro-2-(1H-1,2,4-triazol-1-yl)phenyl]methyl]-1,2,3,5-tetrahydro-6-hydroxy-5-oxo-1-phenyl-imidazo[1,2-a]pyrimidine-7-carboxamide;
N-[[4-fluoro-2-[(methylamino)carbonyl]phenyl]methyl]-1,2,3,5-tetrahydro-6-hydroxy-5-oxo-1-phenyl-imidazo[1,2-a]pyrimidine-7-carboxamide;
N-[(4-fluorophenyl)methyl]-1,2,3,5-tetrahydro-6-hydroxy-1-(1-methylethyl)-5-oxo-imidazo[1,2-a]pyrimidine-7-carboxamide;
N-[(4-fluoro-3-methylphenyl)methyl]-1,2,3,5-tetrahydro-6-hydroxy-1-(1-methylethyl)-5-oxo-imidazo[1,2-a]pyrimidine-7-carboxamide;
N-[[4-fluoro-2-[(methylamino)carbonyl]phenyl]methyl]-1,2,3,5-tetrahydro-6-hydroxy-1-(1-methylethyl)-5-oxo-imidazo[1,2-a]pyrimidine-7-carboxamide;
N-[[4-fluoro-2-(1H-1,2,4-triazol-1-yl)phenyl]methyl]-1,2,3,5-tetrahydro-6-hydroxy-1-(1-methylethyl)-5-oxo-imidazo[1,2-a]pyrimidine-7-carboxamide;
N-[[2-[(dimethylamino)sulfonyl]-4-fluorophenyl]methyl]-1,2,3,5-tetrahydro-6-hydroxy-5-oxo-1-phenyl-imidazo[1,2-a]pyrimidine-7-carboxamide;
N-[[2-[(dimethylamino)sulfonyl]-4-fluorophenyl]methyl]-1,2,3,5-tetrahydro-6-hydroxy-1-(1-methylethyl)-5-oxo-imidazo[1,2-a]pyrimidine-7-carboxamide;
N-[[4-fluoro-2-(3-methyl-1H-1,2,4-triazol-1-yl)phenyl]methyl]-1,2,3,5-tetrahydro-6-hydroxy-5-oxo-1-phenyl-imidazo[1,2-a]pyrimidine-7-carboxamide;
N-[[4-fluoro-2-(5-methyl-1H-1,2,4-triazol-1-yl)phenyl]methyl]-1,2,3,5-tetrahydro-6-hydroxy-5-oxo-1-phenyl-imidazo[1,2-a]pyrimidine-7-carboxamide;
N-[(4-fluorophenyl)methyl]-1,2,3,5-tetrahydro-6-hydroxy-1-(2-hydroxyethyl)-5-oxo-imidazo[1,2-a]pyrimidine-7-carboxamide;
1-butyl-N-[(4-fluorophenyl)methyl]-1,2,3,5-tetrahydro-6-hydroxy-5-oxo-imidazo[1,2-a]pyrimidine-7-carboxamide;
1-butyl-N-[(4-fluoro-3-methylphenyl)methyl]-1,2,3,5-tetrahydro-6-hydroxy-5-oxo-imidazo[1,2-a]pyrimidine-7-carboxamide;
1-butyl-N-[[4-fluoro-2-[(methylamino)carbonyl]phenyl]methyl]-1,2,3,5-tetrahydro-6-hydroxy-5-oxo-imidazo[1,2-a]pyrimidine-7-carboxamide;
1-butyl-N-[[2-[(dimethylamino)sulfonyl]-4-fluorophenyl]methyl]-1,2,3,5-tetrahydro-6-hydroxy-5-oxo-imidazo[1,2-a]pyrimidine-7-carboxamide;
1-cyclohexyl-N-[(4-fluorophenyl)methyl]-1,2,3,5-tetrahydro-6-hydroxy-5-oxo-imidazo[1,2-a]pyrimidine-7-carboxamide;
1-cyclohexyl-N-[(4-fluoro-3-methylphenyl)methyl]-1,2,3,5-tetrahydro-6-hydroxy-5-oxo-imidazo[1,2-a]pyrimidine-7-carboxamide;
1-cyclohexyl-N-[[4-fluoro-2-(1H-1,2,4-triazol-1-yl)phenyl]methyl]-1,2,3,5-tetrahydro-6-hydroxy-5-oxo-imidazo[1,2-a]pyrimidine-7-carboxamide;
1-butyl-N-[[4-fluoro-2-(3-methyl-1H-1,2,4-triazol-1-yl)phenyl]methyl]-1,2,3,5-tetrahydro-6-hydroxy-5-oxo-imidazo[1,2-a]pyrimidine-7-carboxamide;
1-cyclohexyl-N-[[2-[(dimethylamino)sulfonyl]-4-fluorophenyl]methyl]-1,2,3,5-tetrahydro-6-hydroxy-5-oxo-imidazo[1,2-a]pyrimidine-7-carboxamide;
N-[[4-fluoro-2-(2-oxo-1-azetidinyl)phenyl]methyl]-1,2,3,5-tetrahydro-6-hydroxy-5-oxo-1-phenyl-imidazo[1,2-a]pyrimidine-7-carboxamide;
N-[[4-fluoro-2-(1H-1,2,4-triazol-1-yl)phenyl]methyl]-1,2,3,5-tetrahydro-6-hydroxy-1-(2-hydroxyethyl)-5-oxo-imidazo[1,2-a]pyrimidine-7-carboxamide;
N-[[4-fluoro-2-(2-oxo-1-pyrrolidinyl)phenyl]methyl]-1,2,3,5-tetrahydro-6-hydroxy-5-oxo-1-phenyl-imidazo[1,2-a]pyrimidine-7-carboxamide;
N-[(4-fluorophenyl)methyl]-1,2,3,5-tetrahydro-6-hydroxy-1-(2-methoxyethyl)-5-oxo-imidazo[1,2-a]pyrimidine-7-carboxamide;
N-[[4-fluoro-2-(3-methyl-1H-1,2,4-triazol-1-yl)phenyl]methyl]-1,2,3,5-tetrahydro-6-hydroxy-1-(1-methylethyl)-5-oxo-imidazo[1,2-a]pyrimidine-7-carboxamide;
N-[[4-fluoro-2-(5-methyl-1H-1,2,4-triazol-1-yl)phenyl]methyl]-1,2,3,5-tetrahydro-6-hydroxy-1-(1-methylethyl)-5-oxo-imidazo[1,2-a]pyrimidine-7-carboxamide;
N-[[4-fluoro-2-[(methylamino)carbonyl]phenyl]methyl]-1,2,3,5-tetrahydro-6-hydroxy-1-(2-methoxyethyl)-5-oxo-imidazo[1,2-a]pyrimidine-7-carboxamide;
N-[[4-fluoro-2-(1H-1,2,4-triazol-1-yl)phenyl]methyl]-1,2,3,5-tetrahydro-6-hydroxy-1-(2-methoxyethyl)-5-oxo-imidazo[1,2-a]pyrimidine-7-carboxamide;
N-[[2-[(dimethylamino)sulfonyl]-4-fluorophenyl]methyl]-1,2,3,5-tetrahydro-6-hydroxy-1-(2-methoxyethyl)-5-oxo-imidazo[1,2-a]pyrimidine-7-carboxamide;
N-[[4-fluoro-2-(3-methyl-1H-1,2,4-triazol-1-yl)phenyl]methyl]-1,2,3,5-tetrahydro-6-hydroxy-1-(2-methoxyethyl)-5-oxo-imidazo[1,2-a]pyrimidine-7-carboxamide;
N-[[4-fluoro-2-(methylsulfonyl)phenyl]methyl]-1,2,3,5-tetrahydro-6-hydroxy-5-oxo-1-phenyl-imidazo[1,2-a]pyrimidine-7-carboxamide;

1-butyl-N-[[4-fluoro-2-(1H-1,2,4-triazol-1-yl)phenyl]
methyl]-1,2,3,5-tetrahydro-6-hydroxy-5-oxo-imidazo
[1,2-a]pyrimidine-7-carboxamide;

N-[[4-fluoro-2-(methylsulfonyl)phenyl]methyl]-1,2,3,5-
tetrahydro-6-hydroxy-1-(2-methoxyethyl)-5-oxo-imi-
dazo[1,2-a]pyrimidine-7-carboxamide; and

[5-fluoro-2-[[[(1,2,3,5-tetrahydro-6-hydroxy-5-oxo-1-
phenylimidazo[1,2-a]pyrimidin-7-yl)carbonyl]amino]
methyl]phenyl]-phosphonic acid, dimethyl ester;

or a pharmaceutically acceptable salt thereof.

12. A composition comprising a therapeutic amount of a compound of claim 1 and a pharmaceutically acceptable carrier.

13. A method for treating HIV infection comprising administering a therapeutically effective amount of a compound of claim 1, or a pharmaceutically acceptable salt thereof, to a patient in need thereof.

14. The method of claim 13, further comprising a therapeutically effective amount of one or more other HIV treatment agents selected from the group consisting of HIV protease inhibitors, HIV nucleoside reverse transcriptase inhibitors, HIV non-nucleoside reverse transcriptase inhibitors, HIV-entry inhibitors, HIV integrase inhibitors, immunomodulators, or a combination thereof.

* * * * *